United States Patent
Piao et al.

(10) Patent No.: US 10,825,557 B2
(45) Date of Patent: Nov. 3, 2020

(54) MEDICAL INFORMATION PROCESSING APPARATUS

(71) Applicant: Toshiba Medical Systems Corporation, Otawara (JP)

(72) Inventors: Longxun Piao, Nasushiobara (JP); Kousuke Sakaue, Nasushiobara (JP); Masahiro Ozaki, Otawara (JP); Shinya Sugiyama, Nasushiobara (JP); Kei Mori, Shioya (JP)

(73) Assignee: Canon Medical Systems Corporation, Otawara (JP)

( * ) Notice: Subject to any disclaimer, the term of this patent is extended or adjusted under 35 U.S.C. 154(b) by 676 days.

(21) Appl. No.: 15/232,181

(22) Filed: Aug. 9, 2016

(65) Prior Publication Data

US 2017/0068783 A1    Mar. 9, 2017

(30) Foreign Application Priority Data

Sep. 4, 2015 (JP) .................. 2015-174768
Aug. 4, 2016 (JP) .................. 2016-153689

(51) Int. Cl.
G16H 10/60 (2018.01)
G06F 19/00 (2018.01)
G16H 50/70 (2018.01)

(52) U.S. Cl.
CPC .......... *G16H 10/60* (2018.01); *G06F 19/325* (2013.01); *G16H 50/70* (2018.01)

(58) Field of Classification Search
None
See application file for complete search history.

(56) References Cited

U.S. PATENT DOCUMENTS

| 7,711,404 | B2 | 5/2010 | Rao et al. | |
|---|---|---|---|---|
| 8,688,618 | B2* | 4/2014 | McNutt | G06F 19/3481 706/54 |
| 2013/0035956 | A1* | 2/2013 | Carmeli | G06F 19/00 705/3 |
| 2013/0041683 | A1* | 2/2013 | Boissel | G06F 19/12 705/2 |

(Continued)

FOREIGN PATENT DOCUMENTS

JP    2005-509217    4/2005

OTHER PUBLICATIONS

Radiosurgery for recurrent brain metastases . . . , researchgate.net, Gwak et al. (Year: 2009).*

(Continued)

*Primary Examiner* — Dennis W Ruhl
(74) *Attorney, Agent, or Firm* — Oblon, McClelland, Maier & Neustadt, L.L.P.

(57) ABSTRACT

A medical information processing apparatus includes processing circuitry. The processing circuitry acquires information concerning a similar patient similar to a designated patient. The processing circuitry acquires a value representing a first treatment effect and a value representing a first side-effect based on the acquired information concerning the similar patient. The processing circuitry generates a map image in which a mark representing the similar patient is arranged based on the value representing the first treatment effect and the value representing the first side-effect.

17 Claims, 22 Drawing Sheets

(56) References Cited

U.S. PATENT DOCUMENTS

| | | | |
|---|---|---|---|
| 2014/0200954 A1* | 7/2014 | Trifunov | G06Q 50/22 705/7.28 |
| 2014/0244292 A1* | 8/2014 | Rosenberg | G06F 19/324 705/2 |
| 2016/0063212 A1* | 3/2016 | Monier | G06F 19/00 705/3 |
| 2017/0372029 A1* | 12/2017 | Saliman | G16H 10/20 |

OTHER PUBLICATIONS

"Interpreting estimates of treatment affects, implications for managed care", Stephen Faraone, 6 pages (Year: 2008).*
"Patterns of treatment effects in subsets of patients with clinical trials", Bonetti et al., 17 pages (Year: 2004).*

* cited by examiner

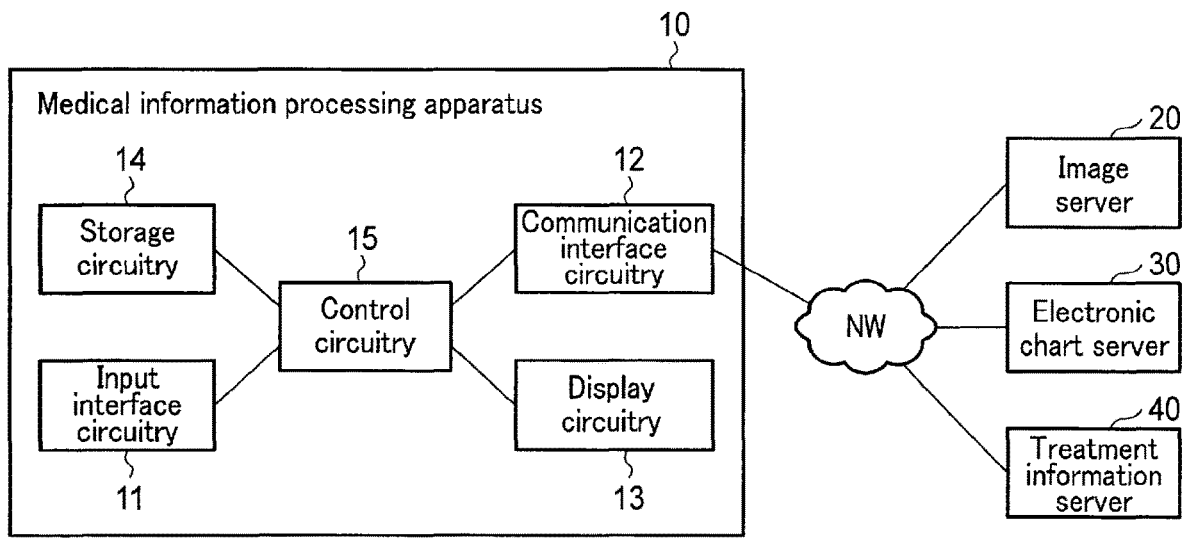
F I G. 1
| Patient ID | Disease name |
|---|---|
| 10000 | Colorectal cancer |
| 10001 | Colorectal cancer |
| 10002 | Colorectal cancer |
| 10003 | Colorectal cancer |
| 10004 | Colorectal cancer |
| 10005 | Colorectal cancer |
| 10006 | Colorectal cancer |
| 10007 | Colorectal cancer |
| 10008 | Esophageal cancer |
| 10067 | Colorectal cancer |
| 10068 | Colorectal cancer |
| ... | ... |
F I G. 2

| Patient ID | Treatment plan number | Treatment result(0~1) | Toxicity (0~1) | Use/nonuse of combined treatment | Resource (treatment cost (ten thousands of yen)) |
|---|---|---|---|---|---|
| 10000 | 1 | 0.30 | 0.40 | Nonuse | 60 |
| 10001 | 2 | 0.70 | 0.30 | Nonuse | 80 |
| 10002 | 3 | 0.60 | 0.70 | Chemotherapy treatment | 50 |
| 10003 | 2 | 0.30 | 0.60 | Chemotherapy treatment | 150 |
| 10004 | 3 | 0.40 | 0.45 | Chemotherapy treatment | 80 |
| 10005 | 1 | 0.20 | 0.60 | Chemotherapy treatment | 90 |
| 10006 | 4 | 0.35 | 0.65 | Chemotherapy treatment | 140 |
| 10007 | 1 | 0.35 | 0.65 | Surgical operation | 80 |
| 10008 | 5 | 0.65 | 0.32 | | |
| 10067 | 1 | | | | |
| 10068 | | | | | |
| ... | ... | | | | |

F I G. 3

| Treatment plan number (Course) | Treatment plan |
|---|---|
| 1 | Three-field irradiation (50 Gy/25 times/4 weeks) |
| 2 | Three-field irradiation (45 Gy/28 times/5 weeks) |
| 3 | Three-field irradiation (40 Gy/20 times/4 weeks) |
| 4 | Four-field irradiation (45 Gy/28 times/4 weeks) |
| 5 | Two-field irradiation (60 Gy/30 times/7 weeks) |

F I G. 4

| Patient ID | Treatment count | Result |
|---|---|---|
| 10067 | Treatment plan generation | Completed |
| 10067 | First-day irradiation | Completed |
| 10067 | Second-day irradiation | Completed |
| 10067 | Third-day irradiation | Completed |
| 10067 | Fourth-day irradiation | Uncompleted |
| 10068 | Treatment plan generation | Uncompleted |
F I G. 5
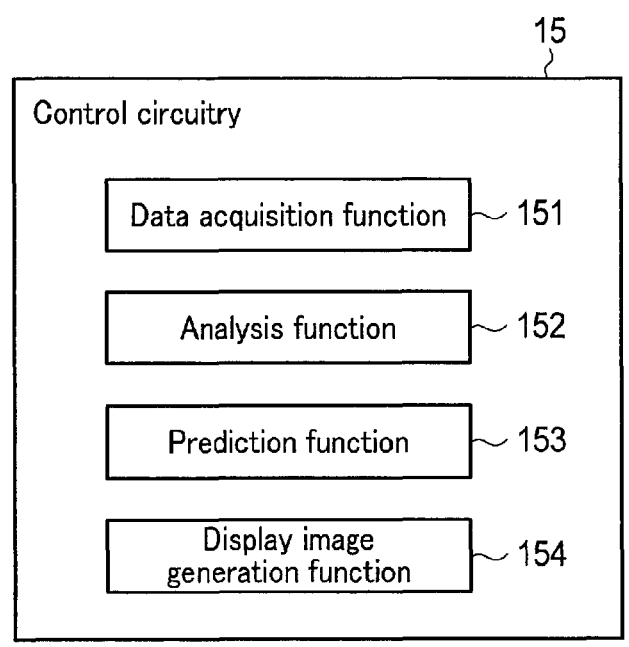
F I G. 6

| Patient ID | Treatment result(0~1) | Toxicity (0~1) |
|---|---|---|
| 10067 | 0.75 | 0.65 |

F I G. 14

| Patient ID | Treatment result(0~1) | Toxicity (0~1) | Use/nonuse of combined treatment | Resource (treatment cost (ten thousands of yen)) |
|---|---|---|---|---|
| 10000 | 0.30 | 0.40 | Nonuse | 60 |
| 10001 | 0.70 | 0.30 | Nonuse | 80 |
| 10002 | 0.60 | 0.70 | Chemotherapy treatment | 50 |
| 10004 | 0.40 | 0.45 | Chemotherapy treatment | 80 |
| 10005 | 0.20 | 0.60 | Chemotherapy treatment | 90 |
| 10006 | 0.35 | 0.65 | Chemotherapy treatment | 140 |
| 10007 | 0.35 | 0.65 | Surgical operation | 80 |

F I G. 15

| Patient ID | Treatment plan number | Treatment result(0~1) | Toxicity (0~1) | Use/nonuse of combined treatment | Resource (treatment cost (ten thousands of yen)) |
|---|---|---|---|---|---|
| 10002 | 3 | 0.60 | 0.70 | Chemotherapy treatment | 50 |
| 10004 | 3 | 0.40 | 0.45 | Chemotherapy treatment | 80 |
| 10005 | 1 | 0.20 | 0.60 | Chemotherapy treatment | 90 |

F I G. 16

| Patient ID | Treatment plan number |
|---|---|
| 10000 | 1 |

| Treatment plan number (Course) | Treatment plan |
|---|---|
| 1 | Three-field irradiation (50 Gy/25 times/4 weeks) |

F I G. 18

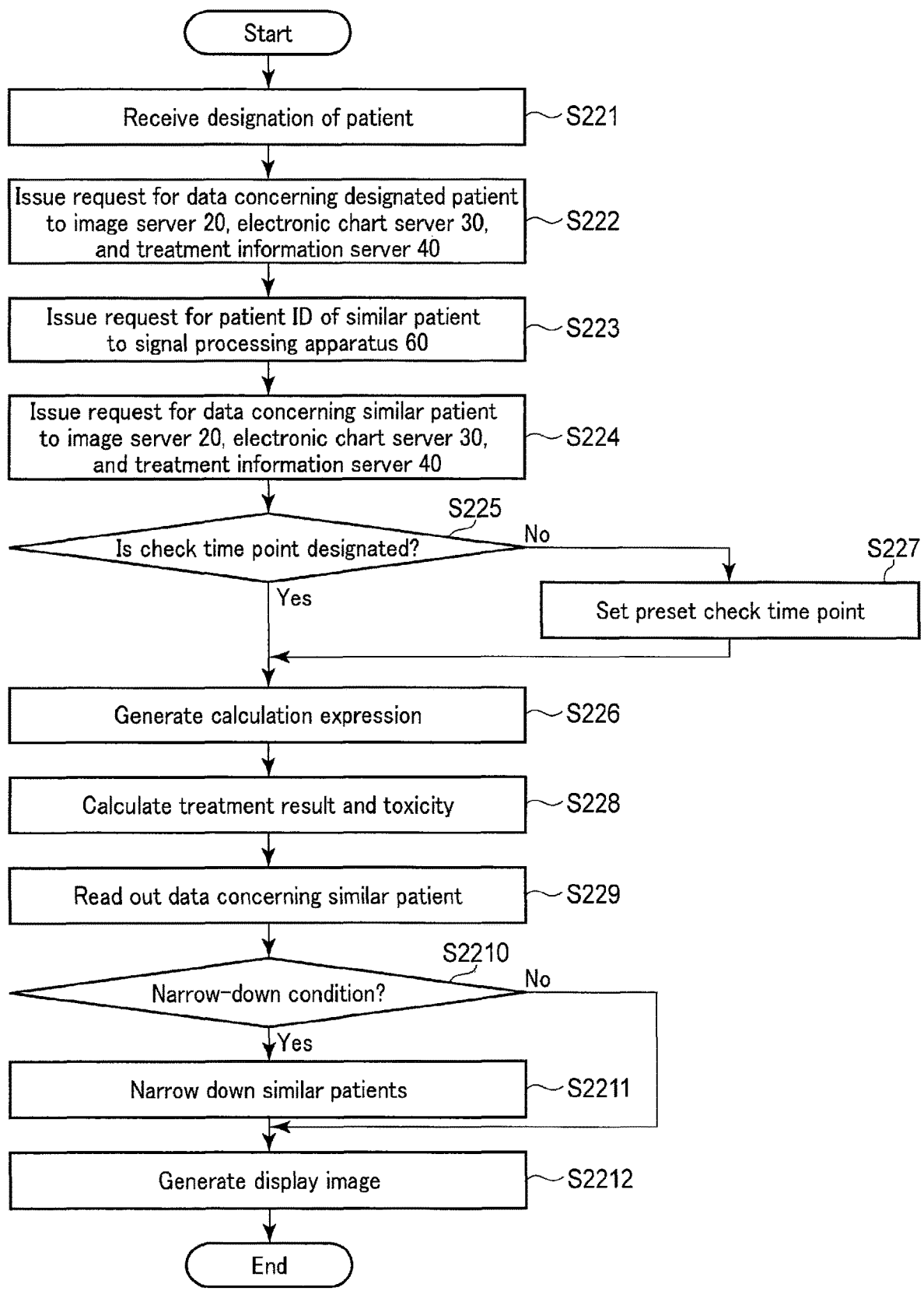
F I G. 22

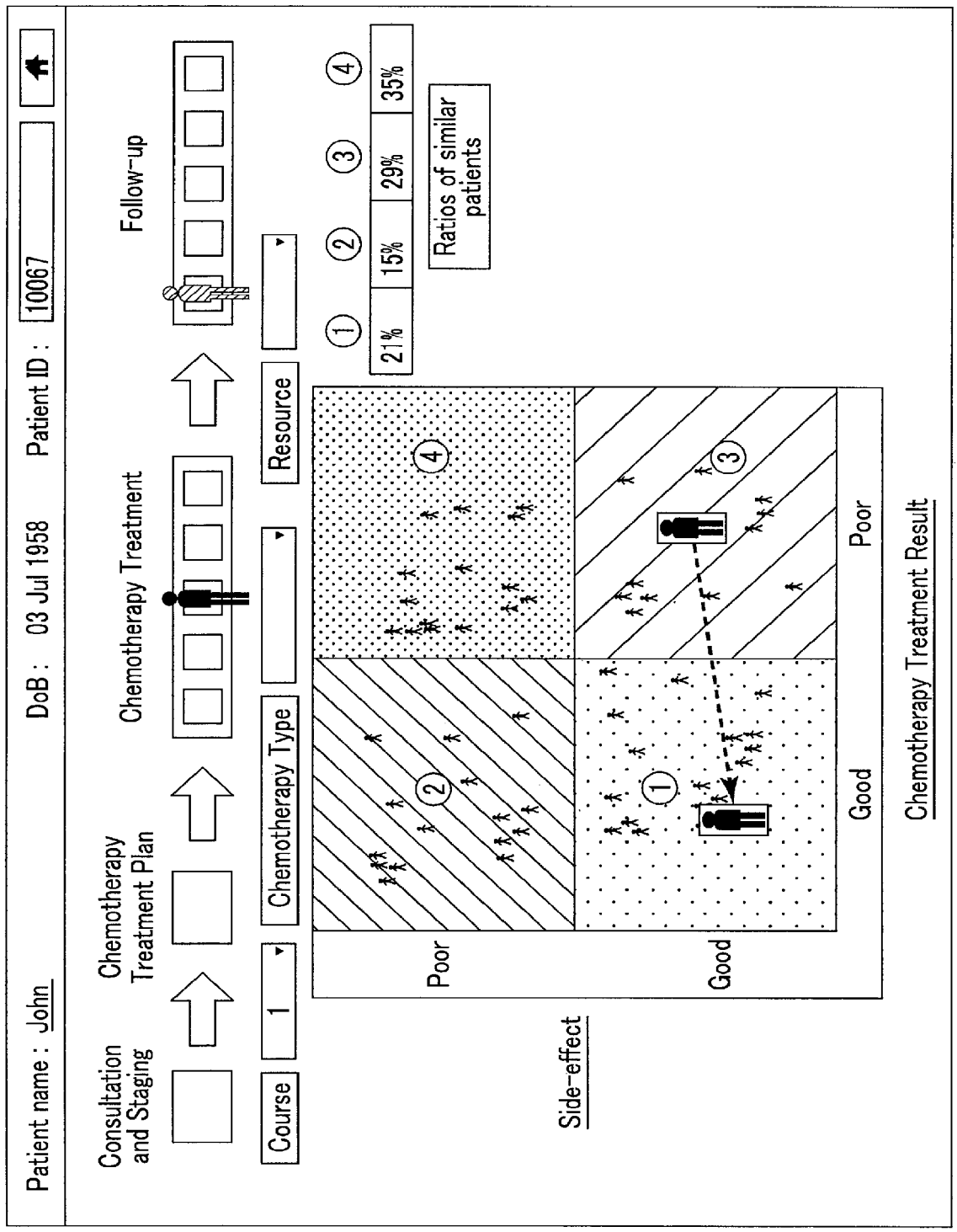
F I G. 27

MEDICAL INFORMATION PROCESSING APPARATUS

CROSS-REFERENCE TO RELATED APPLICATIONS

This application is based upon and claims the benefit of priority from the prior Japanese Patent Application No. 2015-174768, filed Sep. 4, 2015 and No. 2016-153689, filed Aug. 4, 2016, the entire contents of both which are incorporated herein by reference.

FIELD

Embodiments described herein relate generally to a medical information processing apparatus.

BACKGROUND

Recently, there has been proposed a technique of storing medical care information and patient information and deciding a treatment plan for a patient by using these pieces of stored information. It is possible to reduce a load on a patient and efficiently obtain a maximum effect by performing a treatment, medical procedure, and the like based on a treatment plan decided in this manner.

The technique of deciding a treatment plan in the above manner can be applied to a radiotherapy treatment and the like for patients of cancer and the like. In this case, a doctor decides a treatment plan for each patient by referring to expected treatment results and side-effects based on information such as medical care information and patient information. However, in order to derive optimal treatment results and side-effects by using a conventional apparatus which implements this type of technique, the doctor needs to calculate treatment results and side-effects while changing input parameters a plurality of times. This places a burden on the doctor.

BRIEF DESCRIPTION OF THE DRAWING

FIG. 1 is a block diagram showing the arrangement of a medical information system including a medical information processing apparatus according to the first embodiment;

FIG. 2 is a view showing diagnosis data managed by an electronic chart server and a treatment information server shown in FIG. 1;

FIG. 3 is a view showing treatment data managed by an electronic chart server and a treatment information server shown in FIG. 1;

FIG. 4 is a view showing treatment plans managed by the electronic chart server and the treatment information server shown in FIG. 1;

FIG. 5 is a view showing treatment statuses managed by the electronic chart server and the treatment information server shown in FIG. 1;

FIG. 6 is a block diagram showing the functional arrangement of control circuitry shown in FIG. 1;

FIG. 14 is a view showing calculation results on a treatment result and toxicity concerning a designated patient at a check time point;

FIG. 15 is a view showing data concerning similar patients read out from the storage circuitry shown in FIG. 1;

FIG. 16 is a view showing the data of similar patients when the data shown in FIG. 15 is narrowed down;

FIG. 18 is a view showing data concerning a designated similar patient;

FIG. 22 is a flowchart showing a procedure by which the control circuitry shown in FIG. 21 generates a display image;

FIG. 27 is a view showing a case in which the medical information processing apparatus is used to decide a treatment plan for a chemical treatment.

DETAILED DESCRIPTION

Figure 7:
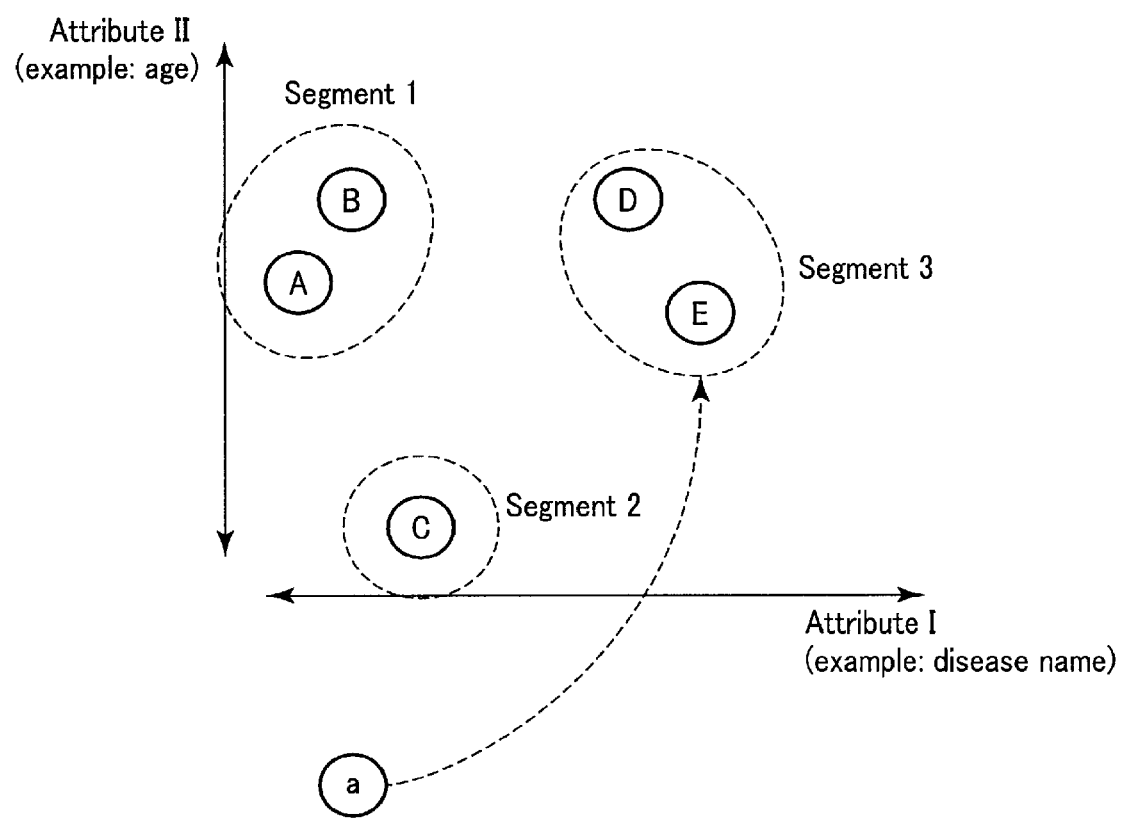
FIG. 7 is a view when the control circuitry shown in FIG. 6 selects similar patients by using an analysis function.

In general, according to one embodiment, a medical information processing apparatus includes processing circuitry. The processing circuitry acquires information concerning a similar patient similar to a designated patient. The processing circuitry acquires a value representing a first treatment effect and a value representing a first side-effect based on the acquired information concerning the similar patient. The processing circuitry generates a map image in which a mark representing the similar patient is arranged based on the value representing the first treatment effect and the value representing the first side-effect.

Embodiments will be described below with reference to the accompanying drawings.

First Embodiment

FIG. 1 is a block diagram showing an example of the arrangement of a medical info/oration system including a medical information processing apparatus 10 according to the first embodiment. The medical information system shown FIG. 1 includes the medical information processing apparatus 10, an image server 20, an electronic chart server 30, and a treatment information server 40. The medical information processing apparatus 10, the image server 20, the electronic chart server 30, and the treatment information server 40 are connected to each other via a network. The network may be a local network provided in a predetermined hospital or an external network connecting an unspecified number of hospitals to each other.

The image server 20 is, for example, one of apparatuses constituting an image management system (PACS: Picture Archiving and Communication System). The image server 20 manages image data according to the DICOM (Digital Imaging and Communication Medicine) specifications and the like.

Image data is output from a medical image diagnostic apparatus (not shown). The medical image diagnostic apparatus is an apparatus which detects an energy signal obtained by interaction with a living body and displays an image of an internal organ or the like. Typical examples of medical image diagnostic apparatuses include an X-ray diagnostic apparatus and X-ray CT apparatus which use X-rays, an MRI (Magnetic Resonance Imaging) using magnetic energy, an ultrasonic diagnostic apparatus using ultrasonic waves, and a nuclear medicine diagnostic apparatus and PET-CT apparatus which use gamma-rays. Note that a cone beam CT and the like are also medical image diagnostic apparatuses.

The electronic chart server 30 and the treatment information server 40 each are one of the apparatuses constituting an HIS (Hospital Information System). The electronic chart server 30 and the treatment information server 40 manage non-image data managed by the hospital information system.

The hospital information system is an information system used in a hospital, and includes, for example, an electronic chart system, receipt computer processing system, ordering system, reception (individual/qualification authentication) system, medical care support system, and department system.

Non-image data includes, for example, patient's basic data, examination data, diagnosis data, treatment data, and finding data.

Patient's basic data includes names, patient IDs, affiliations, birth dates, and sexes which are used to specify medical examinees one by one.

Examination data includes the names of medical institutions which have executed examinations, attending doctor names, examination dates, examination results of examinations executed by medical image diagnostic apparatuses, and numerical values such as body heights, body weights, white blood cell counts, and levels of neutral fat as examination items.

Diagnosis data includes disease names, general statuses, primary lesions, disease stages, pathological tissue types, the progression ranges of disease focuses, the positions of risk organs, pieces of information each indicating a radical treatment or supportive/palliative treatment, the contents of treatments executed in the past, and pieces of information each indicating the use/nonuse of a complication. FIG. 2 is a view showing an example of diagnosis data managed by the electronic chart server 30 and the treatment information server 40. FIG. 2 shows an example of managing diagnosis data by using a table associating patient IDs with disease names.

Treatment data includes treatment plans, treatment statuses, treatment results ("RT Treatment Response"), side-effects such as toxicities ("Toxicity") caused by treatments, pieces of information each indicating the use/nonuse of a combined treatment, and resource management data. Each treatment plan includes a treatment plan number, the irradiation direction of retardation, a dose, a treatment period, and a division count. A treatment status indicates a so-called treatment stage, which represents a specific degree of progress in a treatment plan. Resource management data includes a treatment cost, the time spent by a doctor and a technician, the time spent by nursing, a hospitalization period, the time during which an apparatus was used, and information indicating the use or nonuse of home care facilities.

FIG. 3 is a view showing an example of treatment data managed by the electronic chart server 30 and the treatment information server 40. FIG. 3 shows an example of managing treatment data by using a table associating patient IDs, treatment plan numbers, treatment results, toxicities, pieces of information each indicating the use/nonuse of a combined treatment, and treatment costs. Referring to FIG. 3, each treatment result is represented by a numerical value from 0 to 1. A numerical value closer to 0 indicates a better treatment result. A treatment result is acquired based on the ratio of the volume of a tumor after a radiotherapy treatment to the volume of the tumor before the treatment. In addition, referring to FIG. 3, a toxicity is represented by a numerical value from 0 to 1. A numerical value closer to 0 indicates a better result. A toxicity is acquired based on, for example, a reduction in body weight, QOL (Quality Of Life), T Stage, xerostomia, dysphagia, or the like.

FIG. 4 is a view showing an example of treatment plans managed by the electronic chart server 30 and the treatment information server 40. FIG. 4 shows an example of managing treatment plans by using a table associating treatment plan numbers ("Course"), and treatment plan names.

FIG. 5 is a view showing an example of treatment statuses managed by the electronic chart server 30 and the treatment information server 40. FIG. 5 shows an example of managing treatment statuses by using a table associating patient IDs, treatment counts based on treatment plans, and results indicating whether the corresponding treatment counts have been reached.

Finding data is data input by medical institutions which have executed electrocardiogram examinations, chest X-ray examinations, ultrasonic examinations, and the like. For example, finding data includes information indicating no abnormality and evaluations such as grades A, B, and C.

In addition, non-image data also includes examination order data to the medical image diagnostic apparatus and reports generated when doctors have made diagnoses.

The medical information processing apparatus 10 shown in FIG. 1 includes input interface circuitry 11, communication interface circuitry 12, display circuitry 13, storage circuitry 14, and control circuitry 15.

The input interface circuitry 11 includes, for example, a mouse, keyboard, buttons, panel switches, touch command screen, trackball, and joystick. The input interface circuitry 11 receives various types of instructions, commands, and information input from the operator. The input interface circuitry 11 is connected to the control circuitry 15 via, for example, a bus. The input interface circuitry 11 converts various types of instructions, commands, and information input from the operator into electrical signals, and outputs them to the control circuitry 15. Note that in this specification, the input interface circuitry 11 is not limited to circuitry which includes physical operating components such as a mouse and a keyboard. For example, the input interface circuitry 11 includes, as an example, electrical signal processing circuitry which receives an electrical signal corresponding to an operation instruction input from an external input device provided separately from the medical information processing apparatus 10 and outputs the electrical signal to the control circuitry 15.

The communication interface circuitry 12 accesses the image server 20, the electronic chart server 30, and the treatment information server 40 via a network. The communication interface circuitry 12 receives data supplied from the image server 20, the electronic chart server 30, and the treatment information server 40.

The display circuitry 13 includes a display which displays a display image generated by the control circuitry 15, internal circuitry which supplies a display signal to the display, and peripheral circuitry such as a connector and cable which connect the display to the internal circuitry. As the display unit, for example, an arbitrary display device can be used, such as a CRT display, liquid crystal display, organic EL display, LED display, or plasma display.

The storage circuitry 14 includes a memory which stores electrical information and peripheral circuitry such as a memory controller accompanying the memory, and an interface. The memory includes, for example, a magnetic or optical recording medium or a processor-readable recording medium such as a semiconductor memory. The storage circuitry 14 stores operation programs executed by the medical information processing apparatus 10. The storage circuitry 14 reads out a stored operation program in accordance with a request from the control circuitry 15 provided in the medical information processing apparatus 10.

The storage circuitry 14 also stores non-image data acquired from the electronic chart server 30 and the treatment information server 40 via the communication interface circuitry 12. In addition, the storage circuitry 14 stores check time points input from the input interface circuitry 11. In this embodiment, a check time point is a time point at which it is desired to predict a treatment result and toxicity concerning a patient as a treatment target.

The control circuitry 15 is a processor functioning as the main unit of the medical information processing apparatus 10. The control circuitry 15 reads out an operation program from the storage circuitry 14 and executes the readout operation program to implement a function corresponding to the program. For example, the control circuitry 15 executes operation programs to implement a data acquisition function 151, an analysis function 152, a prediction function 153, and a display image generation function 154 shown in FIG. 6.

The data acquisition function 151 is a function of acquiring non-image data from the electronic chart server 30 and the treatment information server 40. More specifically, the control circuitry 15 executes the data acquisition function 151 to transmit request signals for non-image data to the electronic chart server 30 and the treatment information server 40 via the communication interface circuitry 12. The control circuitry 15 also causes the storage circuitry 14 to store non-image data supplied from the electronic chart server 30 and the treatment information server 40. Note that the control circuitry 15 may transmit request signals to the electronic chart server 30 and the treatment information server 40 at a predetermined cycle or may transmit request signals to the electronic chart server 30 and the treatment information server 40 in accordance with instructions input from the input interface circuitry 11.

The analysis function 152 is a function of selecting patients similar to a designated patient by analyzing non-image data stored in the storage circuitry 14 by using a predetermined data analysis technique. In this case, the predetermined data analysis technique is, for example, data mining. Data mining is an application targeted at finding hidden relevancies and tendencies from a large amount of data. Typical data mining techniques include an association rule, a sequence, a cluster, and a decision tree.

The operation of the control circuitry 15 to be performed when the analysis function 152 is executed will be described in detail below. Upon executing the analysis function 152, the control circuitry 15 reads out data including designated attributes from the storage circuitry 14. The control circuitry 15 reads out data including attributes, e.g., attribute I: age and attribute II: disease name, from the storage circuitry 14.

The control circuitry 15 substitutes data including attributes into a predetermined calculation expression and executes the calculation. The control circuitry 15 classifies patients into a plurality of segments based on calculation results. The control circuitry 15 sets patients belonging to the same segment as similar patients.

FIG. 7 is a schematic view for a case in which the analysis function 152 shown in FIG. 6 selects similar patients. Referring to FIG. 7, the control circuitry 15 respectively sets attribute I and attribute II to "disease name" and "age", and then executes calculation by using information concerning patients A to E and a. With this operation, the control circuitry 15 determines that patients A and B belong to segment 1, patient C belongs to segment 2, and patients D, E, and a belong to segment 3. As a consequence, patients similar to patient a are patients D and E. Although FIG. 7 shows the case in which patients are classified into segments according to two axes as attributes, namely "disease name" and "age". Attributes corresponding to two or more axes may be used, and attributes other than "disease name" and "age" may be used.

The prediction function 153 is a function of predicting a treatment result and toxicity concerning a designated patient at a check time point. More specifically, the control circuitry 15 executes the prediction function 153 to read out data concerning patients similar to the designated patient from the storage circuitry 14. In addition, the control circuitry 15 receives an input of a check time point at which it is desired to predict a treatment result and a toxicity from the input interface circuitry 11. The check time point input at this time is, for example, the nth follow-up time after treatment. Note that n=1, i.e., the first follow-up time after treatment, indicates, for example, a time three months after the completion of a treatment plan. The control circuitry 15 generates a calculation expression for predicting a treatment result and a toxicity at a check time point based on data concerning similar patients. A calculation expression is represented by a function f. The arguments of the function f are x: patient's basic data, y: diagnosis data, and z: treatment data, and outputs from the function f are a treatment result and a toxicity. That is, f(x, y, z)={treatment result, toxicity}.

The control circuitry 15 sets, in the generated calculation expression, values concerning a designated patient, for example, x: patient's basic data {age and sex}, y: diagnosis data {disease name (colorectal cancer)}, and z: treatment data {treatment plan (three-field irradiation (50 Gy/25 times/4 weeks))}. Note that if a designated patient is under treatment, treatment data also includes image information acquired for each treatment and patient information such as a body weight. The control circuitry 15 executes calculation by using the set arguments to calculate a treatment result and a toxicity at the input check time point.

Figure 8:
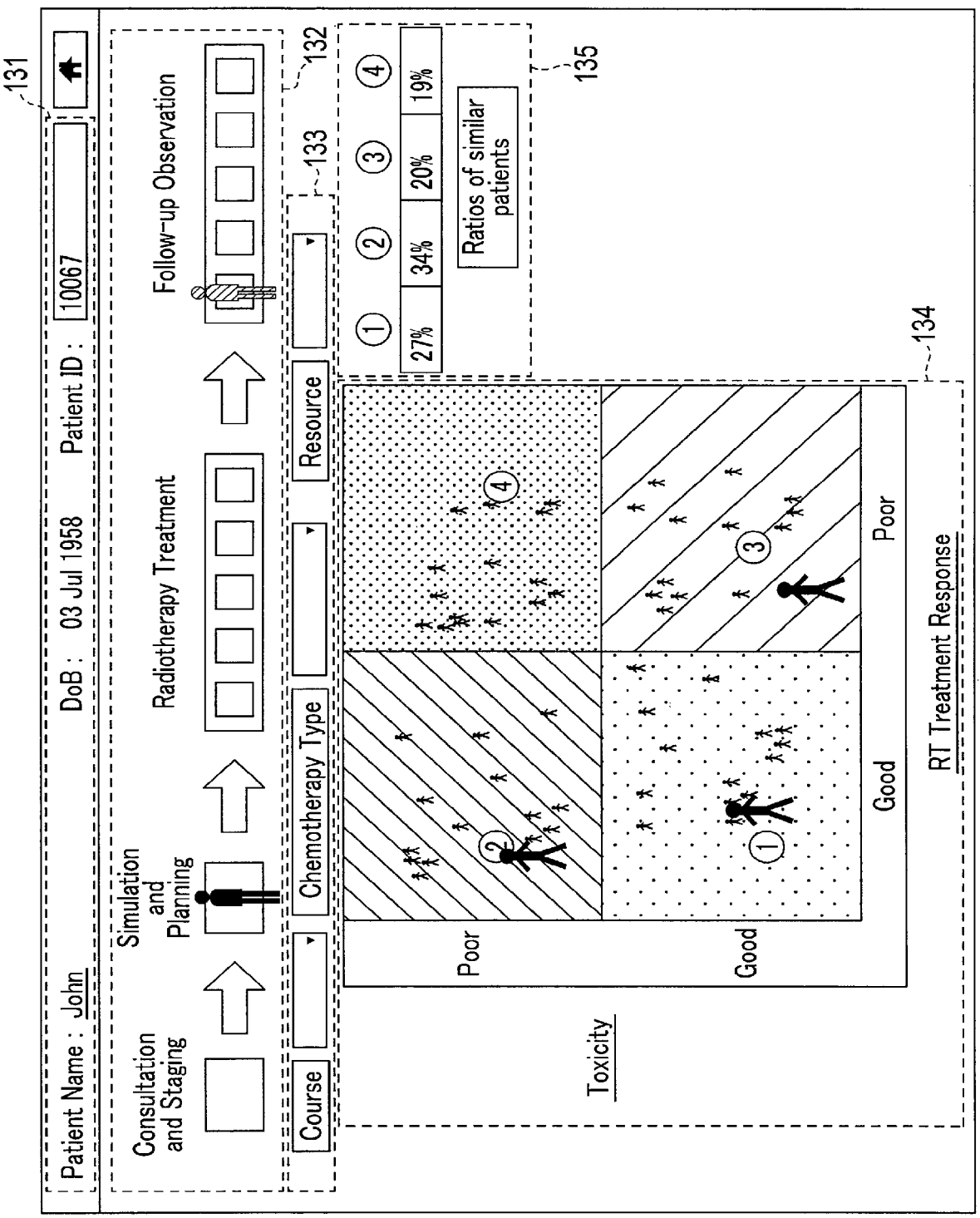
FIG. 8 is a schematic view showing a display image generated by the control circuitry shown in FIG. 6 using a display image generation function.

The display image generation function 154 is a function of generating a display image to be displayed by the display circuitry 13. More specifically, the control circuitry 15 executes the display image generation function 154 to read out treatment results and toxicities concerning similar patients at an input check time point from the storage circuitry 14. The control circuitry 15 generates a display image based on the treatment results and toxicities concerning the similar patients read out from the storage circuitry 14. FIG. 8 is a schematic view showing an example of a display image generated by the display image generation function 154.

Referring to FIG. 8, the display image includes an area 131 for displaying patient's basic information. The patient name, birth date, and patient ID displayed in the area 131 allow the operator to confirm the corresponding patient.

The display image shown in FIG. 8 also includes an area 132 for displaying time points. The area 132 includes the following stages: "Consultation and Staging", "Simulation and Planning", "Radiotherapy Treatment", and "Follow-up Observation". "Consultation and Staging", "Simulation and Planning", and "Radiotherapy Treatment" are time points concerning treatment statuses. "Radiotherapy Treatment" is also provided with steps corresponding to a treatment count included in a treatment status. "Follow-up Observation" is a time point representing a follow-up for treatment. "Follow-up Observation" is further provided with steps corresponding to an examination count after treatment.

The black human figure mark added to the area 132 indicates a time point at which the display image was generated, i.e., the current treatment time point. It is obvious from the example shown in FIG. 8 that this display image was generated at "Simulation and Planning". The hatched human figure mark added to the area 132 indicates a specific time point at which a treatment result and a toxicity were predicted, i.e., a check time point. It is obvious from the example shown in FIG. 8 that this display image is based on the prediction of a treatment result and toxicity in the first step in "Follow-up Observation", i.e., the first examination after treatment. Note that in the example shown in FIG. 8, although the hatched human figure mark indicates a check time point, this is not exhaustive. Any mark indicating a check time point can be used as long as it has a display form different from a mark indicating a treatment time point. For example, a mark indicating a check time point may be a human figure mark in a color different from black, which is the color of the mark indicating a treatment time point.

In addition, the display image shown in FIG. 8 includes an area 133 for inputting narrow-down conditions for narrowing down similar patients. The area 133 includes input boxes concerning "course", "Chemotherapy Type", and "Resource". "Course" represents a treatment plan. "Chemotherapy Type" represents the use/nonuse of a combined treatment. "Resource" represents the type and amount of resource. Narrow-down conditions may be input to two or more of "course", "Chemotherapy Type", and "Resource".

The display image shown in FIG. 8 also includes a two-dimensional area 134, with the X-axis representing treatment result ("RT Treatment response") and the Y-axis representing toxicity ("Toxicity"). In the two-dimensional area 134, good/poor areas are set along dividing lines corresponding to the median values of treatment results and toxicities. With this setting, in the two-dimensional area 134, four quadrants are set, namely a good•good area, a good•poor area, a poor•good area, and a poor•poor area.

The black human figure marks arranged in each area represent similar patients. For example, when treatment results and toxicities each are represented by a numerical value in the range from 0 to 1 in the two-dimensional area 134, each dividing line corresponds to 0.5. In this case, marks representing similar patients corresponding to treatment results and toxicities whose values are both equal to or more than 0 and less than 0.5 are displayed in the good•good area. Marks representing similar patients corresponding to treatment results whose values are equal to or more than 0 and less than 0.5 and toxicities whose values are equal to or more than 0.5 and equal to or less than 1 are displayed in the good•poor area. Marks representing similar patients corresponding to treatment results whose values are equal to or more than 0.5 and equal to or less than 1 and toxicities whose values are equal to or more than 0 and less than 0.5 are displayed in the poor•good area. Marks representing similar patients corresponding to treatment results and toxicities whose values are both equal to or more than 0.5 and equal to or less than 1 are displayed in the poor•poor area. Each black human figure mark is set so as to allow the operator to select it via the input interface circuitry 11.

The black human figure marks arranged in each area include a mark in a display form different from that of the remaining marks. For example, referring to FIG. 8, in each of the good•good area, the good•poor area, and the poor•good area, there is a mark larger than the remaining marks. A similar patient represented by a mark displayed in a different display form in each area represents a similar patient who is progressing most satisfactorily. In this case, a similar patient who is progressing most satisfactorily is a similar patient corresponding to the lowest treatment result value and the lowest toxicity value. Displaying similar patients in different display forms will locate an emphatically displayed similar patient on the outermost side of selectable similar patients. A range whose boundary is represented by an emphatically displayed similar patient group is called a maximum range of selection.

In addition, the display image shown in FIG. 8 includes an area 135 displaying the ratios of similar patients arranged in the respective areas in the two-dimensional area 134. According to the example shown in FIG. 8, the ratio of the similar patients arranged in the good•good area indicated by circle 1 is 27%. The ratio of the similar patients arranged in the good•poor area indicated by circle 2 is 34%. The ratio of the similar patients arranged in the poor•good area indicated by circle 3 is 20%. The ratio of the similar patients arranged in the poor•poor area indicated by circle 4 is 19%. Displaying the ratios in the respective good/poor areas allows an operator such as a doctor to quantitatively check how similar patients are distributed in the good/poor areas.

Figure 9:
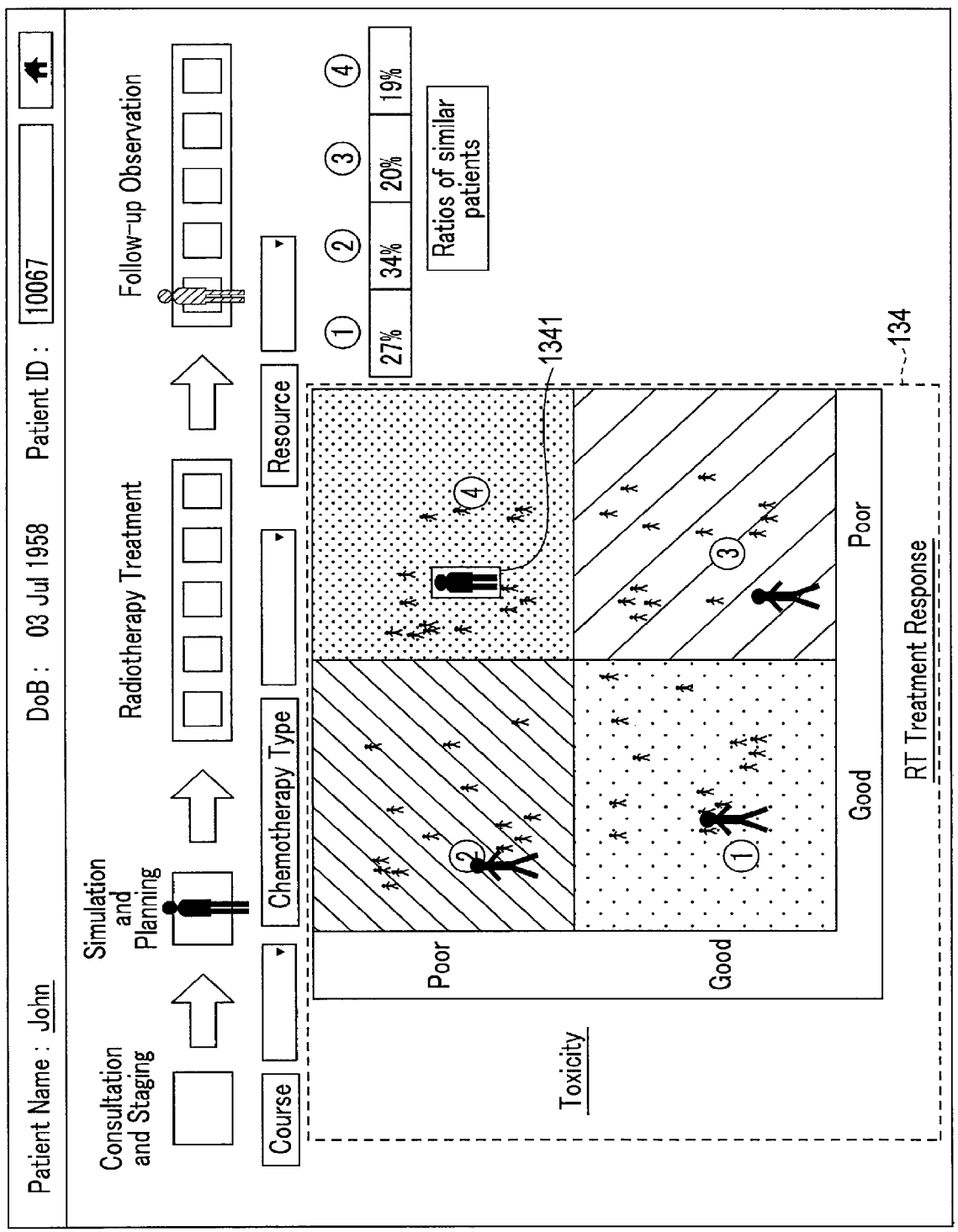
FIG. 9 is a schematic view showing another example of the display image generated by the control circuitry shown in FIG. 6 using the display image generation function.

In addition, the control circuitry 15 may execute the display image generation function 154 to generate a display image based on a predicted treatment result and toxicity concerning a designated patient and treatment results and toxicities concerning similar patients read out from the storage circuitry 14. FIG. 9 is a schematic view showing an example of a display image generated by the display image generation function 154. In the display image shown in FIG. 9, a mark 1341 representing a designated patient is displayed in the two-dimensional area 134 in addition to the display image shown in FIG. 8. The mark 1341 representing the designated patient has a shape different from that of a mark indicating each similar patient. According to the example shown in FIG. 9, the mark 1341 representing the designated patient has a shape which is larger than that of the remaining similar patients and surrounded by a rectangle. Displaying the mark 1341 representing the designated patient in the two-dimensional area 134 allows the operator to evaluate the effect of a treatment plan set for the patient by comparing it with the effects on the similar patients.

The control circuitry 15 executes the display image generation function 154 to generate an image displaying treatment plan data concerning similar patients selected by the operator. More specifically, when the operator issues an instruction to select one of the black human figure marks displayed in the two-dimensional area 134, the control circuitry 15 reads out treatment plan data concerning a similar patient corresponding to the selected mark from the storage circuitry 14. In this case, issuing a selection instruction by the operator is, for example, clicking a black human figure mark displayed in the two-dimensional area 134 by the operator, dragging and dropping a black human figure mark displayed in the two-dimensional area 134 to a designated patient mark, or dragging and dropping a designated patient mark to a black human figure mark. Upon acquiring treatment plan data concerning a selected similar patient, the control circuitry 15 generates an image displaying this treatment plan data. The control circuitry 15 causes the display circuitry 13 to display the generated image.

The control circuitry 15 executes the display image generation function 154 to generate a display image at a past treatment time point. More specifically, when the operator issues an instruction to move, in the direction of past, a black human figure mark added to the area 131 displaying a time point, i.e., "Consultation and Staging", "Simulation and Planning", and "Radiotherapy Treatment", the control circuitry 15 generates a display image at the designated past treatment time point. In this case, issuing an instruction to move a black human figure mark in the direction of past is, for example, clicking of "Consultation and Staging", "Simulation and Planning", or "Radiotherapy Treatment" in the area 131 by the operator or dragging and dropping a black human figure mark added to the area 131 to the left. Note that if the storage circuitry 14 stores display images generated at treatment time points in the past, the control circuitry 15 may read out a past display image from the storage circuitry 14 in accordance with an instruction from the operator.

In addition, the control circuitry 15 executes the display image generation function 154 to generate a display image at a designated check time point. More specifically, when the operator issues an instruction to move a hatched human figure mark added to the area 131 indicating a time point, i.e., "Follow-up Observation", the control circuitry 15 generates a display image at a time point after movement as a check time point. In this case, issuing an instruction to move the hatched human figure mark is, for example, clicking of one of a plurality of steps provided in "Follow-up Observation" which is different from the current state by the operator or dragging and dropping the hatched human figure mark added to the area 131 to one of a plurality of steps provided in "Follow-up Observation" which is different from the current state.

Figure 10:
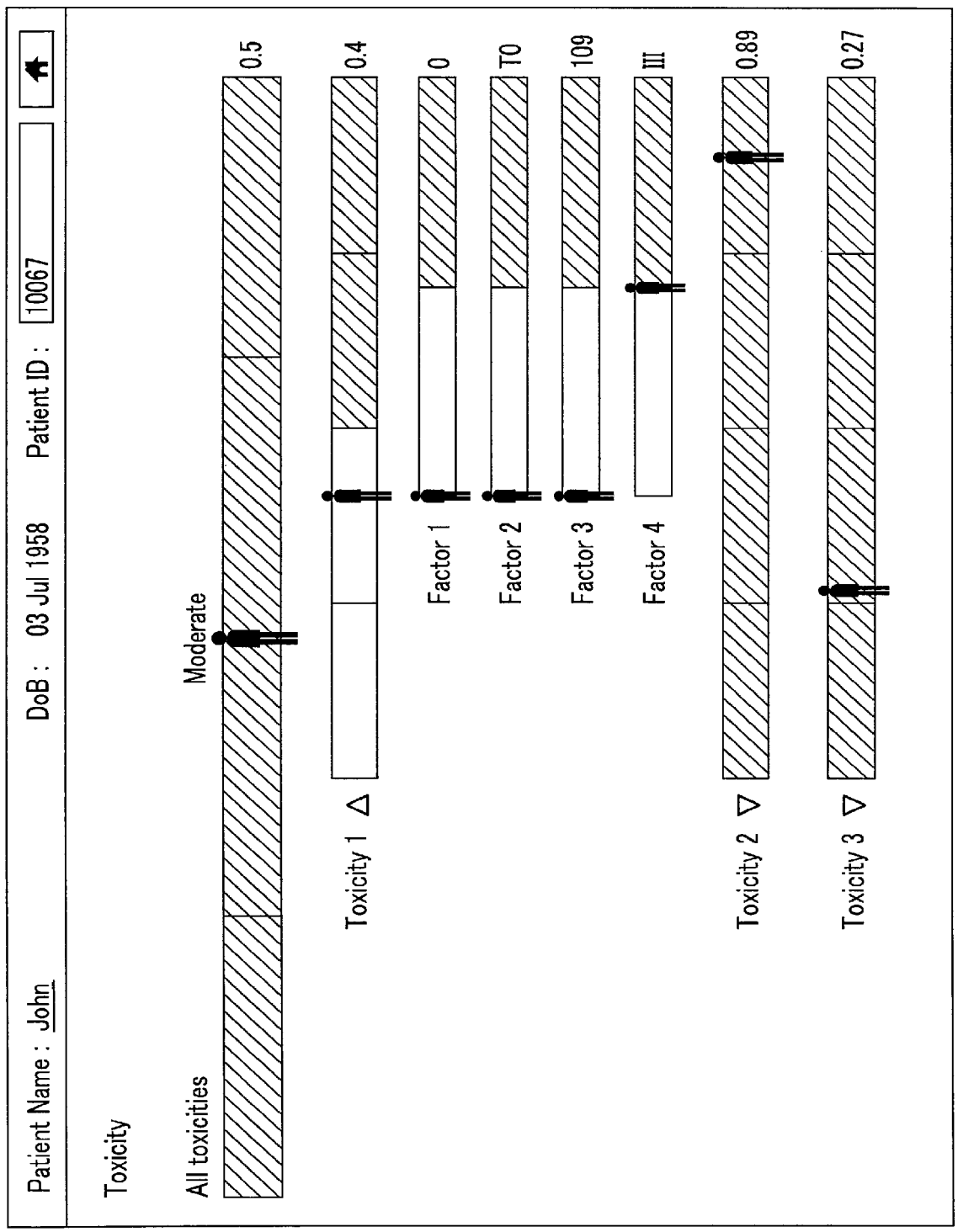
FIG. 10 is a view showing an image displaying detailed data of "Toxicity" shown in FIG. 8.

In addition, the control circuitry 15 executes the display image generation function 154 to generate an image displaying the detailed data of a treatment result or toxicity concerning a selected similar patient. More specifically, when the operator issues a request for the detailed data of toxicity concerning a similar patient, the control circuitry 15 reads out the detailed data of toxicity from the storage circuitry 14. At this time, issuing a request for the detailed data of toxicity is, for example, dragging and dropping a mark indicating a similar patient in the display image to "Toxicity" or double-clicking "Toxicity" while a similar patient is selected. The control circuitry 15 generates an image displaying the detailed data based on the readout detailed data. FIG. 10 is a view showing an example of an image displaying the detailed data of "Toxicity". With reference to FIG. 10, as detailed data, all toxicities and toxicity 1 to toxicity 3 constituting the all toxicities are displayed. When the operator clicks an inverted triangle displayed near "Toxicity", the factors of the toxicity are displayed. FIG. 10 shows a case in which factors 1 to 4 of toxicity 1 are displayed. The control circuitry 15 causes the display circuitry 13 to display a display image concerning the generated detailed data of "Toxicity".

Figure 11:
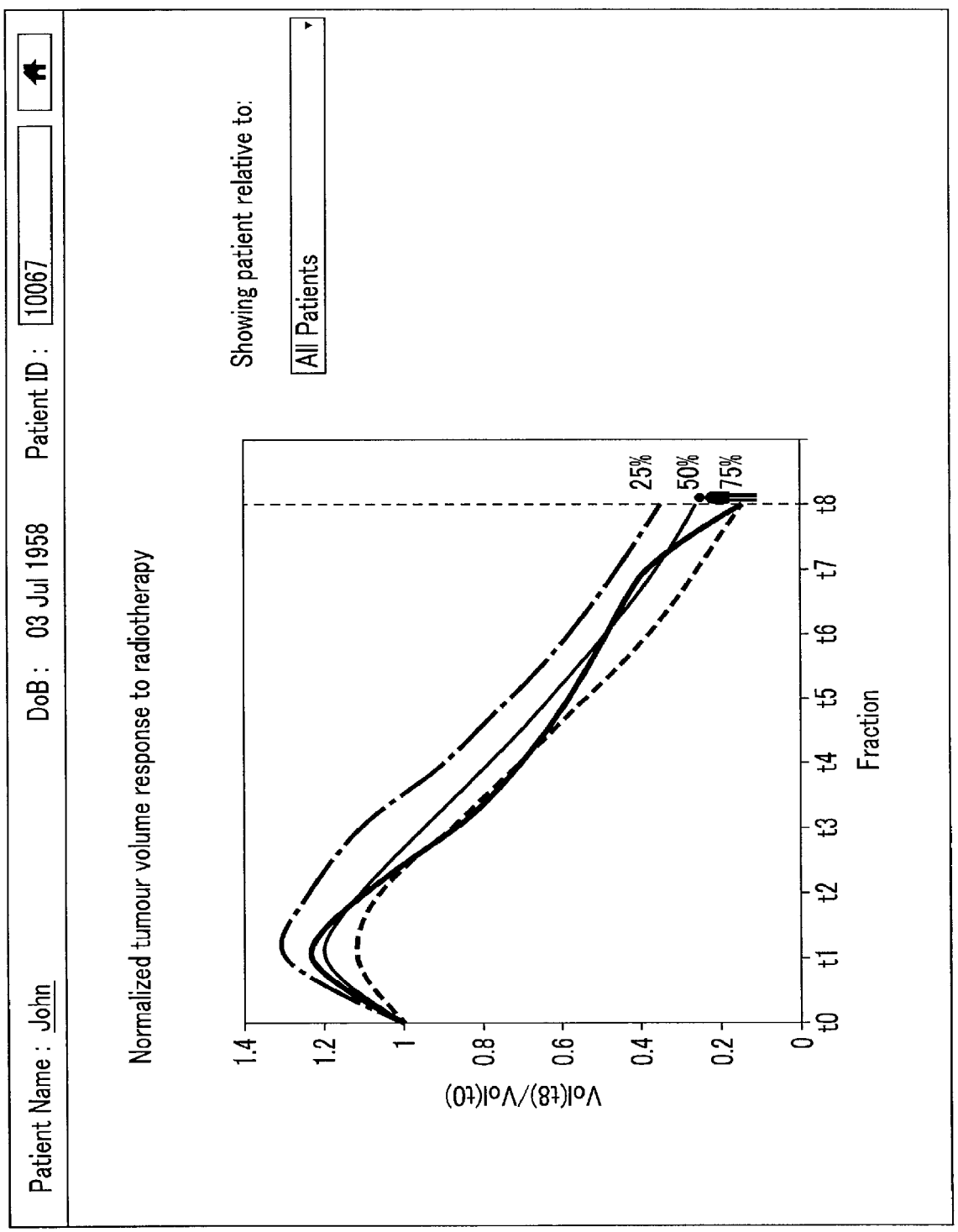
FIG. 11 is a view showing an image displaying the detailed data of "RT Treatment Response" shown in FIG. 8.

In addition, when the operator issues a request for the detailed data of a treatment result concerning a similar patient, the control circuitry 15 reads out the detailed data of the treatment result from the storage circuitry 14. In this case, issuing a request for the detailed data of the treatment result is, for example, dragging and dropping a mark indicating a similar patient in the display image to "RT Treatment Response" or double-clicking "RT Treatment Response" while a similar patient is selected. The control circuitry 15 generates an image displaying the detailed data based on the readout detailed data. FIG. 11 is a view showing an example of an image displaying the detailed data of "RT Treatment Response". Referring to FIG. 11, the abscissa represents an irradiation count of radiation, i.e., a treatment status, and the ordinate represents the ratio of the volume of a tumor after a radiotherapy treatment to the volume of the tumor before the treatment. FIG. 11 shows the transition of a treatment result until t8 times of irradiation of radiation. That is, FIG. 11 shows the detailed data of "RT Treatment Response" concerning similar patients when a time point at which irradiation of radiation has been performed t8 times is input as a check time point. Referring to FIG. 11, the broken line represents the average transition of treatment results concerning upper 25% of similar patients showing good treatment results. The one-dot dashed line represents the average transition of treatment results concerning lower 25% of similar patients showing poor treatment results. The thin solid line represents the average transition of treatment results concerning all the similar patients. The thick solid line represents the transition of treatment results concerning the selected similar patient. The control circuitry 15 causes the display circuitry 13 to display the generated display image concerning the detailed data of "RT Treatment Response".

Figure 12:
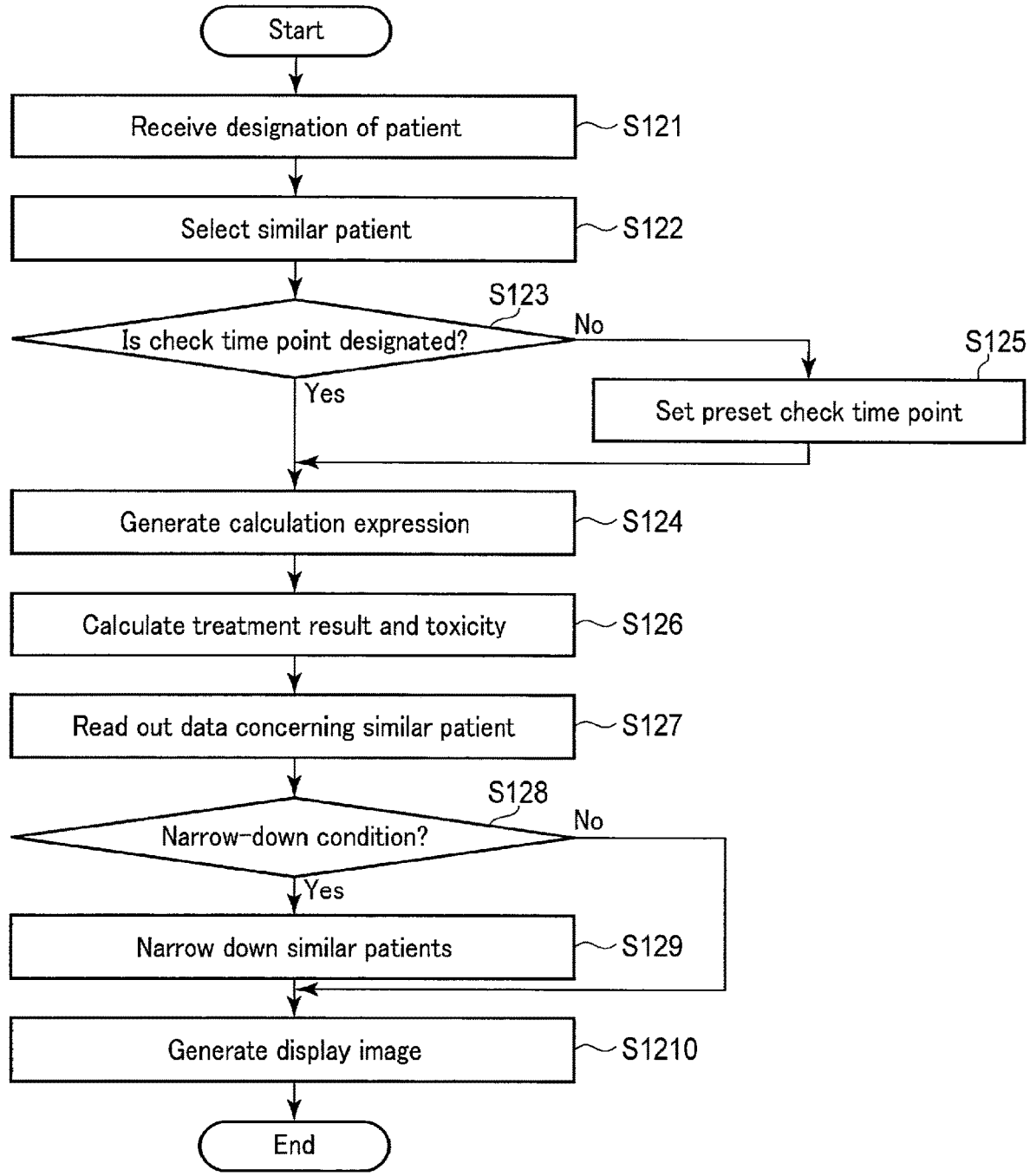
FIG. 12 is a flowchart showing a procedure by which the control circuitry shown in FIG. 6 generates a display image.

The next is a description of the operation of the medical information processing apparatus 10 having the above arrangement when generating a display image. FIG. 12 is a flowchart showing an example of a procedure by which the control circuitry 15 shown in FIGS. 1 to 6 generates a display image.

First of all, the control circuitry 15 receives the designation of a patient (step S121). Upon receiving the designation of a patient, the control circuitry 15 executes the analysis function 152. Upon executing the analysis function 152, the control circuitry 15 decides a segment to which the designated patient belongs. The control circuitry 15 specifies patients similar to the designated patient based on the decided segment (step S122).

Upon specifying similar patients, the control circuitry 15 executes the prediction function 153 and determines whether a check time point is designated (step S123). If a check time point is designated (YES in step S123), the control circuitry 15 generates a calculation expression for predicting a treatment result and a toxicity at the designated check time point based on data concerning the specified similar patients (step S124). If no check time point is designated (NO in step S123), the control circuitry 15 sets, as a check time point, a time point set in advance, for example, the first follow-up time after treatment stored in advance as a designated time point after treatment (step S125), and the process shifts to step S124.

Figure 13:
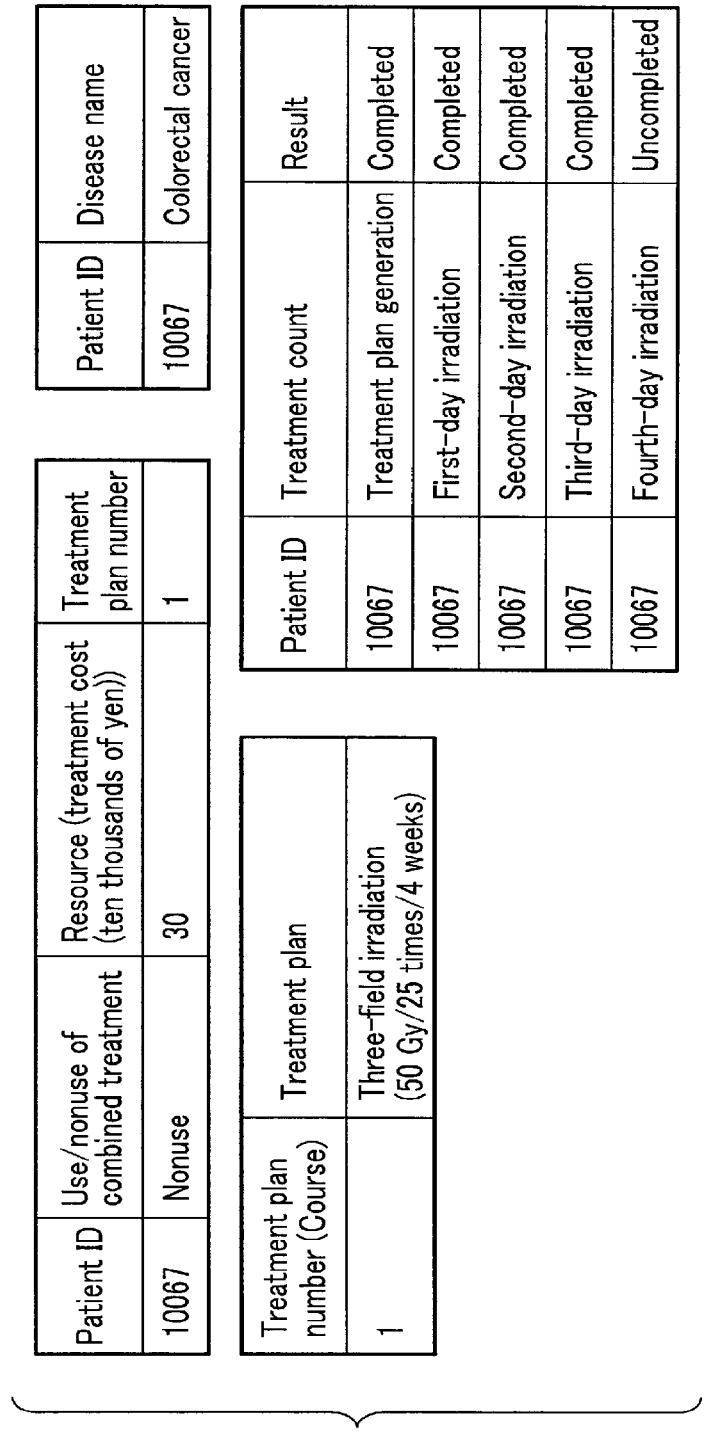
FIG. 13 is a view showing data concerning a designated patient which is read out from storage circuitry shown in FIG. 1.

The control circuitry 15 executes the prediction function 153 to read out data concerning a designated patient from the storage circuitry 14. FIG. 13 is a view showing an example of data concerning the designated patient read out from the storage circuitry 14 when 10067 which is the patient ID of the designated patient is input as a search key. Referring to FIG. 13, the readout data includes treatment data and diagnosis data concerning the designated patient. For the designated patient, as a treatment plan, 1: three-field irradiation (50 Gy/25 times/4 weeks) is selected. In addition, for the designated patient, the selected treatment plan has been completed up to the third-day irradiation. The control circuitry 15 calculates a treatment result and toxicity concerning the designated patient at the check time point by substituting data read out from the storage circuitry 14 into the calculation expression generated in step S124 (step S126). FIG. 14 is a view showing an example of a treatment result and toxicity concerning the designated patient at the check time point.

Upon calculating a treatment result and toxicity concerning the designated patient, the control circuitry 15 executes the display image generation function 154. Upon executing the display image generation function 154, the control circuitry 15 reads out data concerning the similar patients specified in step S122 from the storage circuitry 14 (step S127). FIG. 15 is a view showing an example of data concerning the similar patients read out from the storage circuitry 14. Referring to FIG. 15, the readout data includes patient IDs, treatment results at the check time point, toxicities at the check time point, pieces of information each indicating the use/nonuse of a combined treatment, and treatment costs.

The control circuitry 15 determines whether narrow-down conditions are input via the input interface circuitry 11 (step S128). If narrow-down conditions are input (YES in step S128), the control circuitry 15 extracts similar patients satisfying the input narrow-down conditions (step S129). FIG. 16 shows the data of similar patients extracted from the data shown in FIG. 15 based on the narrow-down conditions "use/nonuse of combined treatment: chemotherapy treatment" and "treatment cost: 1 million yen or less". Referring to FIG. 16, similar patients are narrowed down to the patient IDs "10002", "10004", and "10005". Note that when the narrow-down condition "use/nonuse of combined treatment: chemotherapy treatment" is input with respect to the data shown in FIG. 15, similar patients are narrowed down to the patient IDs "10002", "10004", "10005", and "10006". In addition, when the narrow-down condition "treatment cost: 1 million yen or less" is input with respect to the data shown in FIG. 15, similar patients are narrowed down to the patient IDs "10000", "10001", "10002", "10004", "10005", and "10007".

If no narrow-down condition is input (NO in step S128), the control circuitry 15 shifts the process to the step next to step S129 without narrowing down anything.

The control circuitry 15 generates a display image based on the treatment results and toxicities concerning the similar patients at the check time point (step S1210). More specifically, the control circuitry 15 executes the display image generation function 154 to generate the area 131 displaying patient's basic information based on patient's basic data of a designated patient. In addition, the control circuitry 15 generates the area 132 displaying time points based on a treatment plan and treatment status concerning the designated patient. That is, for example, the control circuitry 15 adds a black human figure mark indicating the current treatment time point to the first step of "Radiotherapy treatment". In addition, the control circuitry 15 generates the area 132 displaying a time point based on a set check time point. That is, for example, the control circuitry 15 adds a hatched human figure mark indicating a check time point to the first step of "Follow-up Observation". Furthermore, the control circuitry 15 generates the area 133 for inputting narrow-down conditions based on input narrow-down conditions.

In addition, the control circuitry 15 reads out treatment results and toxicities at the input check time point concerning narrowed-down similar patients or similar patients having undergone no narrow-down processing from the storage circuitry 14. The control circuitry 15 performs, for example, processing such as scale conversion with respect to the readout treatment results and toxicities and converts them into values suitable for display. The control circuitry 15 decides the display positions of the similar patients in the two-dimensional area 134 based on the treatment results and the toxicities after the conversion.

The control circuitry 15 compares the treatment result and toxicity concerning the designated patient which are predicted at the check time point with the treatment results and toxicities concerning the similar patients. The control circuitry 15 sets, as selectable similar patients, similar patients corresponding to treatment results better than the predicted treatment result and similar patients corresponding to toxicities better than the predicted toxicity. The control circuitry 15 further selects, from the selectable similar patient, similar patients who are progressing most satisfactorily in the good•good area, the good poor area, and the poor•good area. The control circuitry 15 assigns the similar patients who are progressing most satisfactorily in the good•good area, the good poor area, and the poor•good area with marks different from those indicating the remaining similar patients. With this operation, the selected similar patients are emphatically displayed. The control circuitry 15 generates the two-dimensional area 134 based on the decided display positions and the assigned marks.

The control circuitry 15 calculates the ratios of similar patients existing in the respective good/poor areas. The control circuitry 15 generates the area 135 displaying the ratios of the similar patients arranged in the respective areas based on the ratios calculated with respect to the respective good/poor areas.

Figure 17:
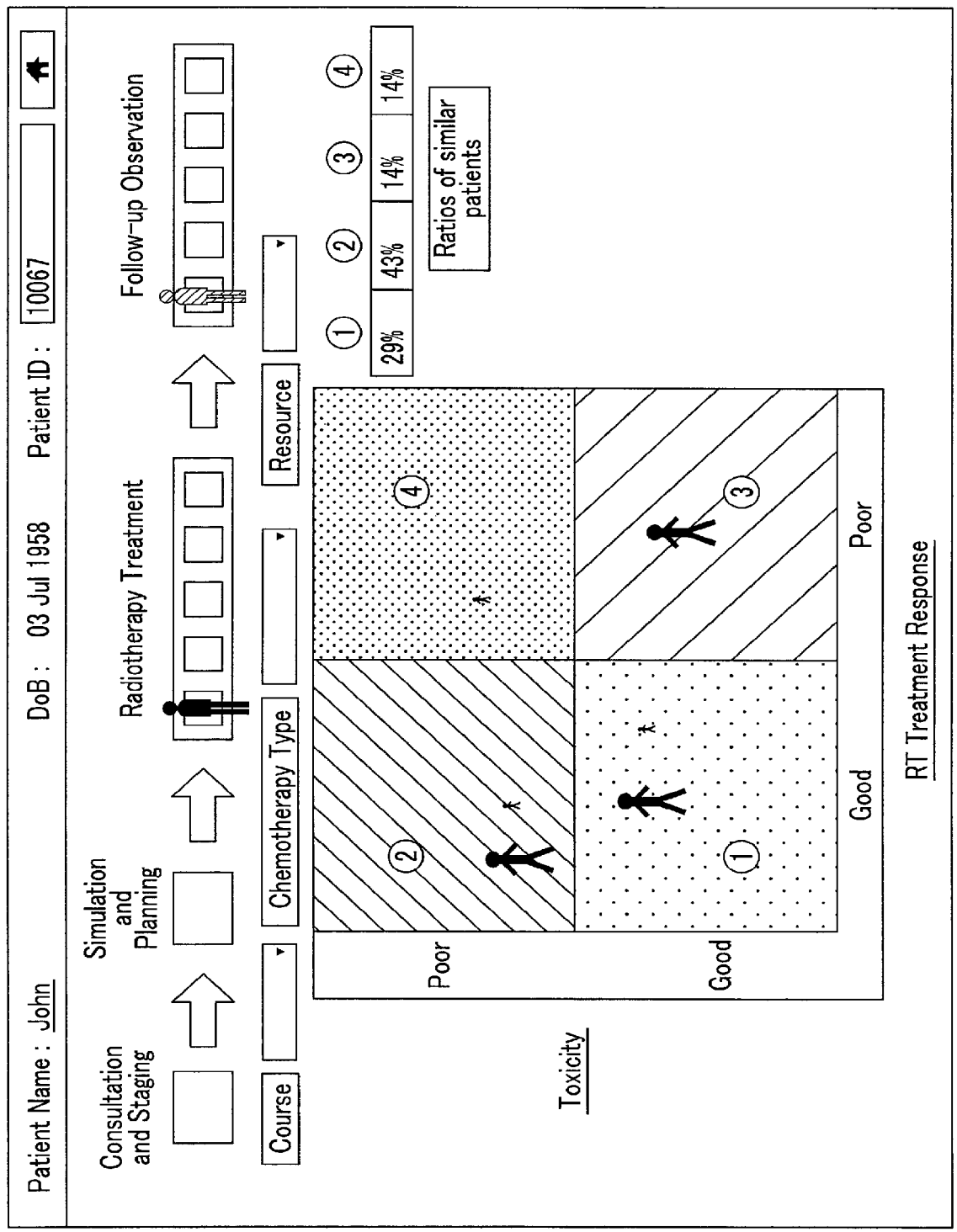
FIG. 17 is a view showing a display image generated under treatment status: third-day irradiation.

FIG. 17 is a view showing an example of a display image concerning the patient ID "10067" with treatment status: third-day irradiation. It is determined, from the black human figure mark added to the leftmost square of "Radiotherapy treatment", that the display image shown in FIG. 17 is a display image generated with treatment status: third-day irradiation. Note that the display image shown in FIG. 17 is a screen generated when a check time point is set to the first follow-up time after treatment and no narrow-down condition is set. In addition, coordinate points indicating treatment results and toxicities concerning the patient ID "10000" indicating the similar patient who is progressing most satisfactorily in the good•good area, the patient ID "10005" indicating the similar patient who is progressing most satisfactorily in the good•poor area, and the patient ID "10001" indicating the similar patient who is progressing most satisfactorily in the poor•good area are assigned with marks larger than those indicating the remaining similar patients.

When the operator who sees the display circuitry 13 selects the patient ID "10000" indicating the similar patient who is progressing most satisfactorily in the good•good area, the control circuitry 15 executes the display image generation function 154. The control circuitry 15 reads out data concerning the patient ID "10000" from the storage circuitry 14. FIG. 18 is a view showing an example of data concerning the patient ID "10000" read out by the control circuitry 15. Referring to FIG. 18, the control circuitry 15 acquires treatment plan number: 1 from the treatment data table by using the patient ID "10000" as a search key, and acquires three-field irradiation (50 Gy/25 times/4 weeks) from treatment plan number: 1. The control circuitry 15 generates a display image based on the acquired data. The control circuitry 15 causes the display circuitry 13 to display the generated display image.

Figure 19:
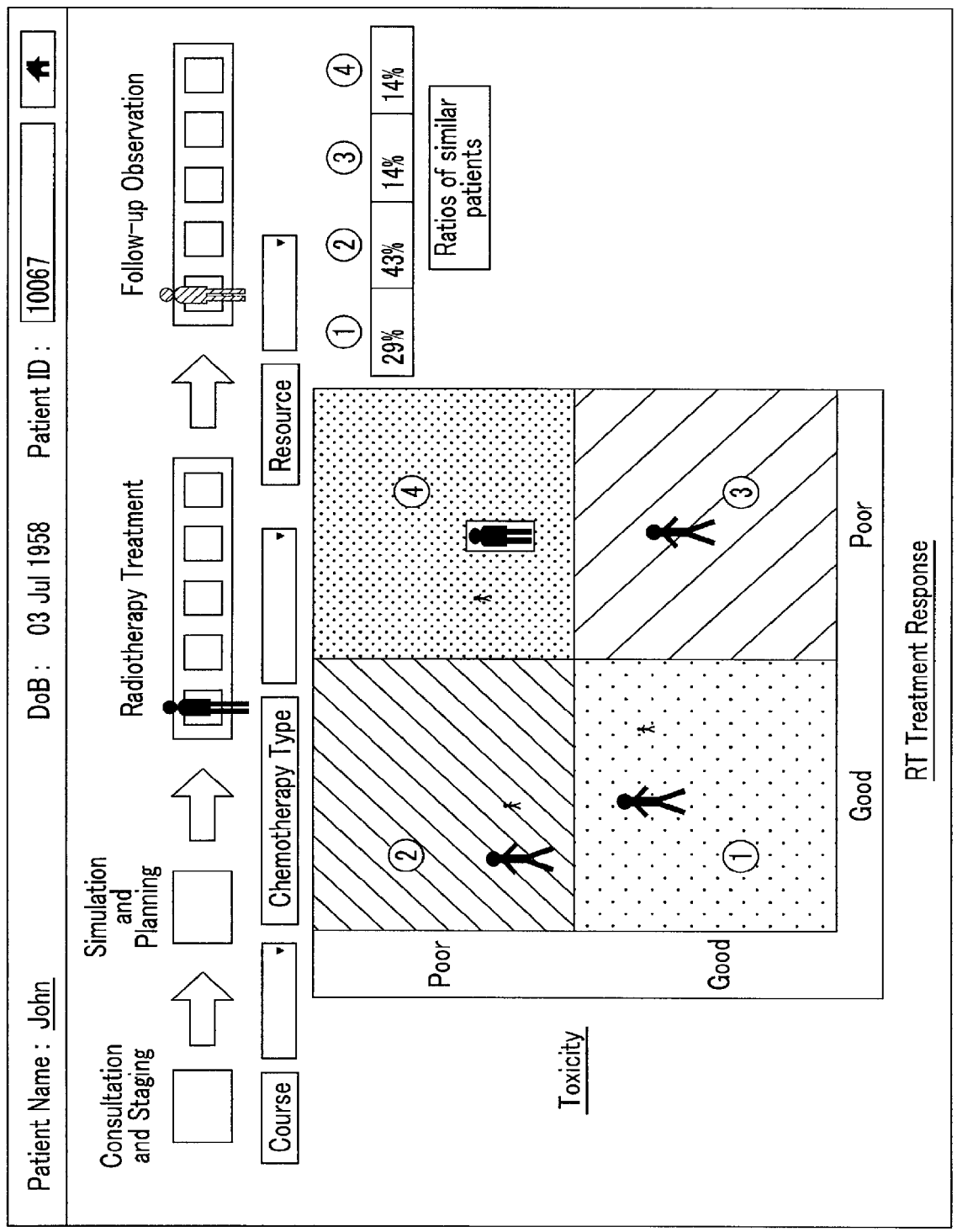
FIG. 19 is a view showing another example of the display image generated under treatment status: third-day irradiation.

Note that the flowchart shown in FIG. 12 is used to explain a case in which the control circuitry 15 generates the display image shown in FIG. 17. However, this is not exhaustive. The control circuitry 15 may generate, in step S1210, the display image shown in FIG. 19 based on the treatment result and toxicity concerning the designated patient at the check time point and the treatment results and toxicities concerning the similar patients at the check time point. In the display image shown in FIG. 19, in addition to the display image shown in FIG. 17, the mark indicating the designated patient is displayed in the two-dimensional area 134.

As described above, in the first embodiment, the control circuitry 15 executes the analysis function 152 to select similar patients similar in set attributes to a designated patient. The control circuitry 15 then executes the display image generation function 154 to generate a two-dimensional map with axes respectively representing treatment result and toxicity and display similar patients corresponding to a designated patient on the two-dimensional map.

The related art includes a technique capable of simulating a treatment result and a toxicity by using diagnosis data concerning a patient and treatment data for a treatment plan. However, a doctor needs to simulate a treatment result and a toxicity while changing values in a treatment plan based on his/her experience. For this reason, the doctor needs to perform checking work repeatedly, resulting in an increase in burden on the doctor. In addition, it is sometimes difficult to derive an optimal treatment plan and toxicity.

In contrast to this, the medical information processing apparatus 10 according to the first embodiment displays similar patients corresponding to a designated patient on a two-dimensional map with axes respectively representing treatment result and toxicity. This allows the medical information processing apparatus 10 to make the operator select an optimal treatment result and toxicity which can lead to the designated patient from the similar patients displayed on the two-dimensional map. That is, an operator such as a doctor need not simulate treatment results and toxicities while changing input parameters a plurality of times to acquire an optimal treatment result and toxicity.

The medical information processing apparatus 10 according to the first embodiment, therefore, allows a doctor as an operator to easily select an optimal treatment result and side-effect and decide a treatment plan in accordance with the selected treatment result and side-effect.

In addition, according to the first embodiment, the control circuitry 15 executes the prediction function 153 to generate a calculation expression for predicting a treatment result and a toxicity at a designated check time point based on selected similar patients. The control circuitry 15 calculates a treatment result and a toxicity concerning the designated patient by using the generated calculation expression. The control circuitry 15 then executes the display image generation function 154 to display a designated patient and similar patients on a two-dimensional map. This allows the medical information processing apparatus 10 to make the operator select an optimal treatment result and a toxicity which can lead to the designated patient while comparing the designated patient with the similar patients displayed on the two-dimensional map.

In addition, according to the first embodiment, the control circuitry 15 executes the display image generation function 154 to generate a display image displaying a treatment plan concerning a designated similar patient on a two-dimensional map. This allows the medical information processing apparatus 10 to easily acquire treatment plan concerning a similar patient which can be expected to lead to an optimal treatment result and toxicity concerning the designated patient.

In addition, according to the first embodiment, the control circuitry 15 executes the prediction function 153 to predict a treatment result and a toxicity, when a designated patient is under treatment, by using treatment results and toxicities acquired during the treatment. The related art cannot support decision whether to change a treatment plan during a treatment. In contrast to this, the medical information processing apparatus 10 according to the first embodiment predicts a treatment result and a toxicity by also using treatment results and toxicities acquired during a treatment, and hence can support decision in consideration of measurement results during the treatment.

In addition, the first embodiment is configured to manage resource management data, included in treatment data, including treatment costs, the times spent by doctors and technicians, the times spent for nursing, hospitalization periods, the times during which apparatuses were used, and information indicating the use or nonuse of home care facilities. The control circuitry 15 then executes the display image generation function 154 to narrow down similar patients in accordance with narrow-down conditions set with respect to the resource management data. Conventionally, it has been impossible to make a treatment plan in consideration of the viewpoint of resource management. In contrast to this, the medical information processing apparatus 10 according to this embodiment narrows down similar patients based on resource management data, and hence can make a treatment plan in consideration of the viewpoint of resource management.

Note that the first embodiment has exemplified the case in which the control circuitry 15 executes the analysis function 152 to select similar patients by using data mining. However, this is not exhaustive. The control circuitry 15 may execute the analysis function 152 to use other statistical techniques such as correlation and regression analysis, time-series analysis, multidimensional analysis, and simulation.

In addition, according to the first embodiment, the control circuitry 15 executes the data acquisition function 151 to acquire non-image data stored in the electronic chart server 30 and the treatment information server 40. The embodiment has exemplified the case in which the control circuitry 15 selects patients similar to a designated patient by analyzing the non-image data by using a predetermined data analysis technique. However, this is not exhaustive. The control circuitry 15 may execute the data acquisition function 151 to extract necessary data from the image data stored in the image server 20. In this case, the storage circuitry 14 stores the data extracted by the control circuitry 15. The control circuitry 15 then executes the analysis function 152 to select patients similar to the designated patient by analyzing the non-image data and the extracted data by using a predetermined data analysis technique.

In addition, according to the first embodiment, the control circuitry 15 executes the analysis function 152 to classify patients into segments with two axes and set patients belonging to the same segment as similar patients. The embodiment has exemplified the case in which the control circuitry 15 then executes the prediction function 153 to generate a calculation expression for predicting a treatment result and a toxicity at a check time point based on data concerning selected similar patients. However, this is not exhaustive. For example, the control circuitry 15 may execute the analysis function 152 to select two types of similar patients. The first similar patients are selected to allow a more effective treatment by comparing treatment results and toxicities with those of a designated patient. The second similar patients are selected to predict a treatment result and a toxicity at a check time point. Note that pieces of information of the second similar patients are similar in more attributes than pieces of information of the first similar patients. The control circuitry 15 executes the prediction function 153 to generate a calculation expression for predicting a treatment result and a toxicity at a check time point based on data concerning selected second similar patients.

Second Embodiment

The first embodiment has exemplified the case in which the medical information processing apparatus 10 selects similar patients. However, an apparatus other than the medical information processing apparatus 10 may select similar patients.

Figure 20:
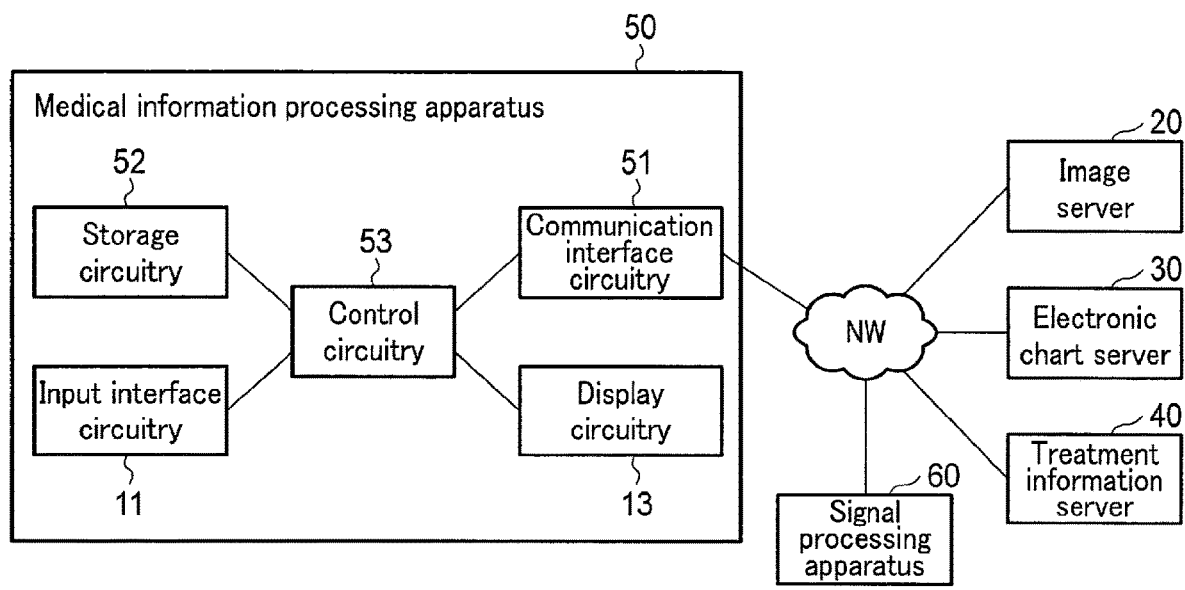
FIG. 20 is a block diagram showing the arrangement of a medical information system including a medical information processing apparatus according to the second embodiment.

FIG. 20 is a block diagram showing the arrangement of a medical information system including a medical information processing apparatus 50 according to the second embodiment. The medical information system shown in FIG. 20 includes the medical information processing apparatus 50, a signal processing apparatus 60, an image server 20, an electronic chart server 30, and a treatment information server 40. The medical information processing apparatus 50, the signal processing apparatus 60, the image server 20, the electronic chart server 30, and the treatment information server 40 are connected to each other via a network.

The signal processing apparatus 60 includes a processor which executes predetermined processing. The signal processing apparatus 60 classifies patients into a plurality of segments by analyzing data extracted from the image data stored in the image server 20 and non-image data stored in the electronic chart server 30 and the treatment information server 40 by using a predetermined data analysis technique. In this case, the predetermined data analysis technique includes, for example, data mining and a statistical technique.

When a patient is designated by a patient ID presented from the medical information processing apparatus 50, the signal processing apparatus 60 sets patients belonging to the same segment as that of a designated patient as similar patients, and outputs the patient IDs of the similar patients to the medical information processing apparatus 50.

The medical information processing apparatus 50 includes input interface circuitry 11, communication interface circuitry 51, display circuitry 13, storage circuitry 52, and control circuitry 53.

The communication interface circuitry 51 accesses the signal processing apparatus 60, the image server 20, the electronic chart server 30, and the treatment information server 40 via the network. The communication interface circuitry 51 receives data supplied from the signal processing apparatus 60, the image server 20, the electronic chart server 30, and the treatment information server 40.

The storage circuitry 52 includes a memory which stores electrical information and peripheral circuitry such as a memory controller accompanying the memory, and an interface. The memory includes, for example, a magnetic or optical recording medium or a processor-readable recording medium such as a semiconductor memory. The storage circuitry 52 stores operation programs executed by the medical information processing apparatus 50. The storage circuitry 52 reads out a stored operation program in accordance with a request from the control circuitry 53 provided in the medical information processing apparatus 50.

The storage circuitry 52 also stores data acquired from the image server 20, the electronic chart server 30, and the treatment information server 40 via the communication interface circuitry 51. In addition, the storage circuitry 52 stores check time points input from the input interface circuitry 11.

Figure 21:
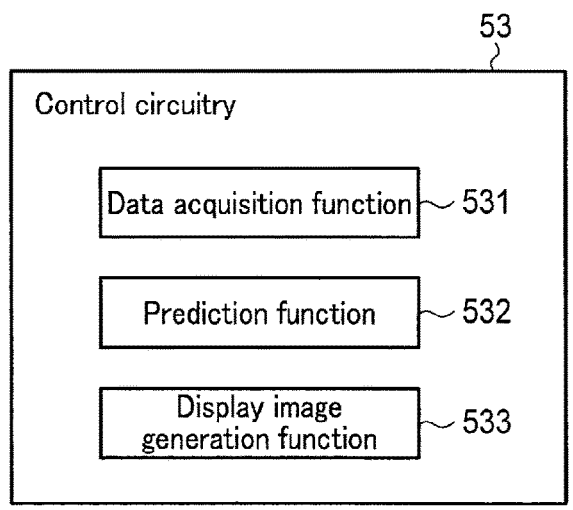
FIG. 21 is a block diagram showing the functional arrangement of control circuitry shown in FIG. 20.

The control circuitry 53 is a processor functioning as the main unit of the medical information processing apparatus 50. The control circuitry 53 reads out an operation program from the storage circuitry 52 and executes the readout operation program to implement a function corresponding to the program. For example, the control circuitry 53 executes operation programs to implement a data acquisition function 531, a prediction function 532, and a display image generation function 533 shown in FIG. 21.

The data acquisition function 531 is a function of acquiring data concerning a designated patient from the image server 20, the electronic chart server 30, and the treatment information server 40. More specifically, the control circuitry 53 executes the data acquisition function 531 to designate a patient by, for example, presenting a patient ID with respect to the image server 20, the electronic chart server 30, and the treatment information server 40, and issues a request for data concerning the designated patient. The control circuitry 53 receives data concerning the designated patient from the image server 20, the electronic chart server 30, and the treatment information server 40, and causes the storage circuitry 52 to store the received data.

In addition, the control circuitry 53 executes the data acquisition function 531 to designate a patient by, for example, presenting a patient ID with respect to the signal processing apparatus 60 and issue a request for the patient IDs of patients similar to the designated patient. The control circuitry 53 receives the patient IDs of the similar patients from the signal processing apparatus 60 and causes the storage circuitry 52 to store the received data.

The prediction function 532 is a function of predicting a treatment result and toxicity concerning a designated patient at a check time point. More specifically, the control circuitry 53 executes the prediction function 532 to read out data concerning a designated patient and data concerning patients similar to the designated patient from the storage circuitry 52. In addition, the control circuitry 53 receives an input of a check time point at which it is desired to predict a treatment result and a toxicity from the input interface circuitry 11. The control circuitry 53 generates a calculation expression for predicting a treatment result and a toxicity at a check time point based on the data concerning the similar patients.

The control circuitry 53 sets, in the generated calculation expression, values concerning a designated patient. The control circuitry 53 executes calculation by using set arguments to calculate a treatment result and a toxicity at the input check time point.

The display image generation function 533 is a function of generating a display mage to be displayed by the display circuitry 13. More specifically, the control circuitry 53 executes the display image generation function 533 to read out a treatment result and toxicity concerning similar patients at an input check time point from the storage circuitry 52. The control circuitry 53 generates a display image based on a predicted treatment result and toxicity and the treatment results and toxicities concerning the similar patients read out from the storage circuitry 52. The control circuitry 53 causes the display circuitry 13 to display the generated display image.

The control circuitry 53 executes the display image generation function 533 to generate an image displaying treatment plan data concerning similar patients selected by the operator. More specifically, when the operator issues an instruction to select one of the black human figure marks displayed in a two-dimensional area 134, the control circuitry 53 reads out treatment plan data concerning similar patients corresponding to the selected mark from the storage circuitry 52. Upon acquiring treatment plan data concerning selected similar patients, the control circuitry 53 generates an image displaying this treatment plan data. The control circuitry 53 causes the display circuitry 13 to display the generated image.

The control circuitry 53 executes the display image generation function 533 to generate a display image at a past treatment time point. More specifically, when the operator issues an instruction to move, in the direction of past, a black human figure mark added to an area 131 displaying a time point, the control circuitry 53 generates again a display image at the designated past treatment time point. Note that the control circuitry 53 may cause the storage circuitry 52 to store the display image generated at the past treatment time point, and read out the stored past display image in accordance with an instruction from the operator.

In addition, the control circuitry 53 executes the display image generation function 533 to generate a display image at a designated check time point. More specifically, when the operator issues an instruction to move a hatched human figure mark added to the area 131 indicating a time point, the control circuitry 53 generates a display image at a time point after movement as a check time point.

In addition, the control circuitry 53 executes the display image generation function 533 to generate an image displaying the detailed data of treatment results or toxicities concerning selected similar patients. More specifically, when the operator issues a request for the detailed data of toxicities concerning similar patients, the control circuitry 53 reads out the detailed data of toxicities from the storage circuitry 52. The control circuitry 53 generates an image displaying the detailed data based on the readout detailed data. The control circuitry 53 causes the display circuitry 13 to display a display image concerning the generated detailed data of "Toxicity".

In addition, when the operator issues a request for the detailed data of treatment results concerning similar patients, the control circuitry 53 reads out the detailed data of the treatment results from the storage circuitry 52. The control circuitry 53 generates an image displaying the detailed data based on the readout detailed data. The control circuitry 53 causes the display circuitry 13 to display the generated display image concerning the detailed data of "RT Treatment Response".

The next is a description of the operation of the medical information processing apparatus 50 having the above arrangement when generating a display image. FIG. 22 is a flowchart showing an example of a procedure by which the control circuitry 53 shown in FIGS. 20 and 21 generates a display image.

First of all, the control circuitry 53 receives the designation of a patient, e.g., an input of a patient ID (step S221). Upon receiving the designation of a patient, the control circuitry 53 executes the data acquisition function 531. The control circuitry 53 executes the data acquisition function 531 to issue a request for data concerning the designated patient to the image server 20, the electronic chart server 30, and the treatment information server 40 by transmitting a patient ID to the image server 20, the electronic chart server 30, and the treatment information server 40 (step S222). Upon receiving data concerning the designated patient transmitted from the image server 20, the electronic chart server 30, and the treatment information server 40 in accordance with the request, the control circuitry 53 causes the storage circuitry 52 to store the received data.

The control circuitry 53 issues a request for the patient IDs of patients similar to the designated patient to the signal processing apparatus 60 (step S223). Upon receiving the patient IDs of the similar patients transmitted from the signal processing apparatus 60 in accordance with the request, the control circuitry 53 causes the storage circuitry 52 to store the received data. The control circuitry 53 issues requests for data concerning the similar patients to the image server 20, the electronic chart server 30, and the treatment information server 40 by transmitting the patient IDs of the similar patients to the image server 20, the electronic chart server 30, and the treatment information server 40 (step S224). Upon receiving data concerning the similar patients transmitted from the image server 20, the electronic chart server 30, and the treatment information server 40 in accordance with the requests, the control circuitry 53 causes the storage circuitry 52 to store the received data.

Subsequently, the control circuitry 53 executes the prediction function 532 to determine whether a check time point is designated (step S225). If a check time point is designated (YES in step S225), the control circuitry 53 generates a calculation expression for predicting treatment results and toxicities at the designated check time point based on data concerning the similar patients (step S226). If no check time point is designated (NO in step S225), the control circuitry 53 sets a check time point to be set in advance (step S227). The process then shifts to step S226.

The control circuitry 53 executes the prediction function 532 to read out data concerning a designated patient from the storage circuitry 52. The control circuitry 53 calculates a treatment result and toxicity concerning the designated patient at the check time point by substituting the data read out from the storage circuitry 52 into the calculation expression generated in step S226 (step S228).

Upon calculating a treatment result and toxicity concerning the designated patient, the control circuitry 53 executes the display image generation function 533. Upon executing the display image generation function 533, the control circuitry 53 reads out data concerning the similar patients from the storage circuitry 52 (step S229).

The control circuitry 53 determines whether narrow-down conditions are input via the input interface circuitry 11 (step S2210). If narrow-down conditions are input (YES in step S810), the control circuitry 53 extracts similar patients satisfying the input narrow-down conditions from the readout similar patients (step S2211). If no narrow-down condition is input (NO in step S2210), the control circuitry 53 shifts the process to the step next to step S2211 without narrowing down anything.

The control circuitry 53 generates a display image based on the treatment results and toxicities concerning the similar patients at the check time point (step S2212). More specifically, the control circuitry 53 executes the display image generation function 533 to generate an area 131 displaying patient's basic information based on patient's basic data of a designated patient. In addition, the control circuitry 53 generates an area 132 displaying time points based on a treatment plan and treatment status concerning the designated patient. In addition, the control circuitry 53 generates the area 132 displaying a time point based on a set check time point. Furthermore, the control circuitry 53 generates an area 133 for inputting narrow-down conditions based on input narrow-down conditions.

In addition, the control circuitry 53 reads out treatment results and toxicities at the input check time point concerning narrowed-down similar patients or similar patients having undergone no narrow-down processing from the storage circuitry 52. The control circuitry 53 performs, for example, processing such as changing the scale with respect to the readout treatment results and toxicities and converts them into values suitable for display. The control circuitry 53 decides the display positions of the similar patients in the two-dimensional area 134, with the X-axis representing treatment result and the Y-axis representing toxicity, based on the treatment results and the toxicities after the conversion.

The control circuitry 53 compares the treatment result and toxicity concerning the designated patient which are predicted at the check time point with the treatment results and toxicities concerning the similar patients. The control circuitry 53 sets, as selectable similar patients, similar patients corresponding to treatment results better than the predicted treatment result and similar patients corresponding to toxicities better than the predicted toxicity. The control circuitry 53 further selects, from the selectable similar patient, similar patients who are progressing most satisfactorily in the good•good area, the good•poor area, and the poor•good area. The control circuitry 53 assigns the similar patients who are progressing most satisfactorily in the good•good area, the good•poor area, and the poor•good area with marks different from those indicating the remaining similar patients. The control circuitry 53 generates the two-dimensional area 134 based on the decided display positions and the assigned marks.

The control circuitry 53 calculates the ratios of similar patients existing in the respective good/poor areas. The control circuitry 53 generates an area 135 displaying the ratios of the similar patients arranged in the respective areas based on the ratios calculated with respect to the respective good/poor areas. With the above processing, for example, the display image shown in FIG. 17 is generated.

As described above, according to the second embodiment, the control circuitry 53 executes the display image generation function 533 to generate a two-dimensional map, with axes respectively representing treatment result and toxicity, and display similar patients selected by the signal processing apparatus 60 on the two-dimensional map. This allows the medical information processing apparatus 50 according to the second embodiment to make the operator select an optimal treatment result and toxicity which can lead to the designated patient from the similar patients displayed on the two-dimensional map. That is, an operator such as a doctor need not simulate treatment results and toxicities while changing input parameters a plurality of times to acquire an optimal treatment result and toxicity.

The medical information processing apparatus 50 according to the second embodiment, therefore, allows a doctor as an operator to easily select an optimal treatment result and side-effect and decide a treatment plan in accordance with the selected treatment result and side-effect.

In addition, according to the second embodiment, the control circuitry 53 executes the prediction function 532 to generate a calculation expression for predicting a treatment result and a toxicity at a designated check time point based on selected similar patients selected by the signal processing apparatus 60. The control circuitry 53 calculates a treatment result and a toxicity concerning a designated patient by using the generated calculation expression. The control circuitry 53 then executes the display image generation function 533 to display a designated patient and similar patients on a two-dimensional map. This allows the medical information processing apparatus 50 to make the operator select an optimal treatment result and toxicity which can lead to the designated patient while comparing the designated patient with the similar patients displayed on the two-dimensional map.

In addition, according to the second embodiment, the control circuitry 53 executes the display image generation function 533 to generate a display image displaying a treatment plan concerning a designated similar patient on a two-dimensional map. This allows the medical information processing apparatus 50 to easily acquire a treatment plan concerning a similar patient which can be expected to obtain an optimal treatment result and toxicity concerning the designated patient.

In addition, according to the second embodiment, the control circuitry 53 executes the prediction function 532 to predict a treatment result and a toxicity, when a designated patient is under treatment, by using treatment results and toxicities acquired during the treatment. This allows the medical information processing apparatus 50 according to the second embodiment to support decision in consideration of measurement results during the treatment.

In addition, the second embodiment is configured to manage resource management data, included in treatment data, including treatment costs, the times spent by doctors and technicians, the times spent for nursing, hospitalization periods, the times during which apparatuses were used, and information indicating the use or nonuse of home care facilities. The control circuitry 53 then executes the display image generation function 533 to narrow down similar patients in accordance with narrow-down conditions set with respect to the resource management data. This allows the medical information processing apparatus 50 according to the second embodiment to make a treatment plan in consideration of the viewpoint of resource management.

Other Embodiments

The first or second embodiment has exemplified the case in which the control circuitry 15 or 53 executes the display image generation function 154 or 533 to generate a display image by predicting a treatment result and toxicity concerning a designated patient at a check time point based on the current treatment time point. However, this is not exhaustive. For example, the control circuitry 15 or 53 may express a change from the first display image generated at a past treatment time point to the second display image generated at the current treatment time point on the second display image. For example, this change is displayed in the following manner.

First of all, when generating the first display image at the first treatment time point in the past, the control circuitry 15 or 53 causes the storage circuitry 14 or 52 to store a predicted treatment result and toxicity concerning a designated patient. Upon issuance of an instruction to generate the second display image at the second treatment time point, the control circuitry 15 or 53 generates the second display image at a check time point based on the second treatment time point. Note that the second display image includes a mark indicating the state of the designated patient predicted based on the state of the designated patient at the second treatment time point and the maximum range of selection drawn based on the states of similar patients at a check time point which are read out based on conditions input at the second treatment time point.

Subsequently, the control circuitry 15 or 53 expresses a change from the first display image to the second display image on the second display image. For example, the control circuitry 15 or 53 acquires information concerning similar patients read out at the first treatment time. The control circuitry 15 or 53 decides the positions of the similar patients in the second display image by referring to the acquired treatment results and toxicities concerning the similar patients. The control circuitry 15 or 53 selects similar patients, of the similar patients whose positions have been decided, which are located on the outermost side, and connects the selected similar patients with a line. The line connecting the selected similar patients indicates the maximum range of selection.

The control circuitry 15 or 53 decides the position of the designated patient in the second display image by referring to the treatment result and toxicity concerning the designated patient which are predicted at the first treatment time point. The control circuitry 15 or 53 superimposes, on the second display image, the maximum range of selection concerning the first treatment time point and a mark indicating the position of the designated patient concerning the first treatment time point. In addition, the control circuitry 15 or 53 superimposes, on the second display image, an arrow indicating the movement of the maximum range of selection and an arrow indicating the movement of the designated patient. Note that a method of acquiring the maximum range of selection concerning the first treatment time point is not limited to the above method. For example, the control circuitry 15 or 53 may store, as image data, a line indicating the maximum range of selection expressed on the first display image generated at the first treatment time point, and may read out the image data when generating the second display image at the second treatment time point. Furthermore, the indication of the movement of the maximum range of selection and the indication of the movement of the designated patient are not limited to arrows as long as it is possible to express movement.

Figure 23:
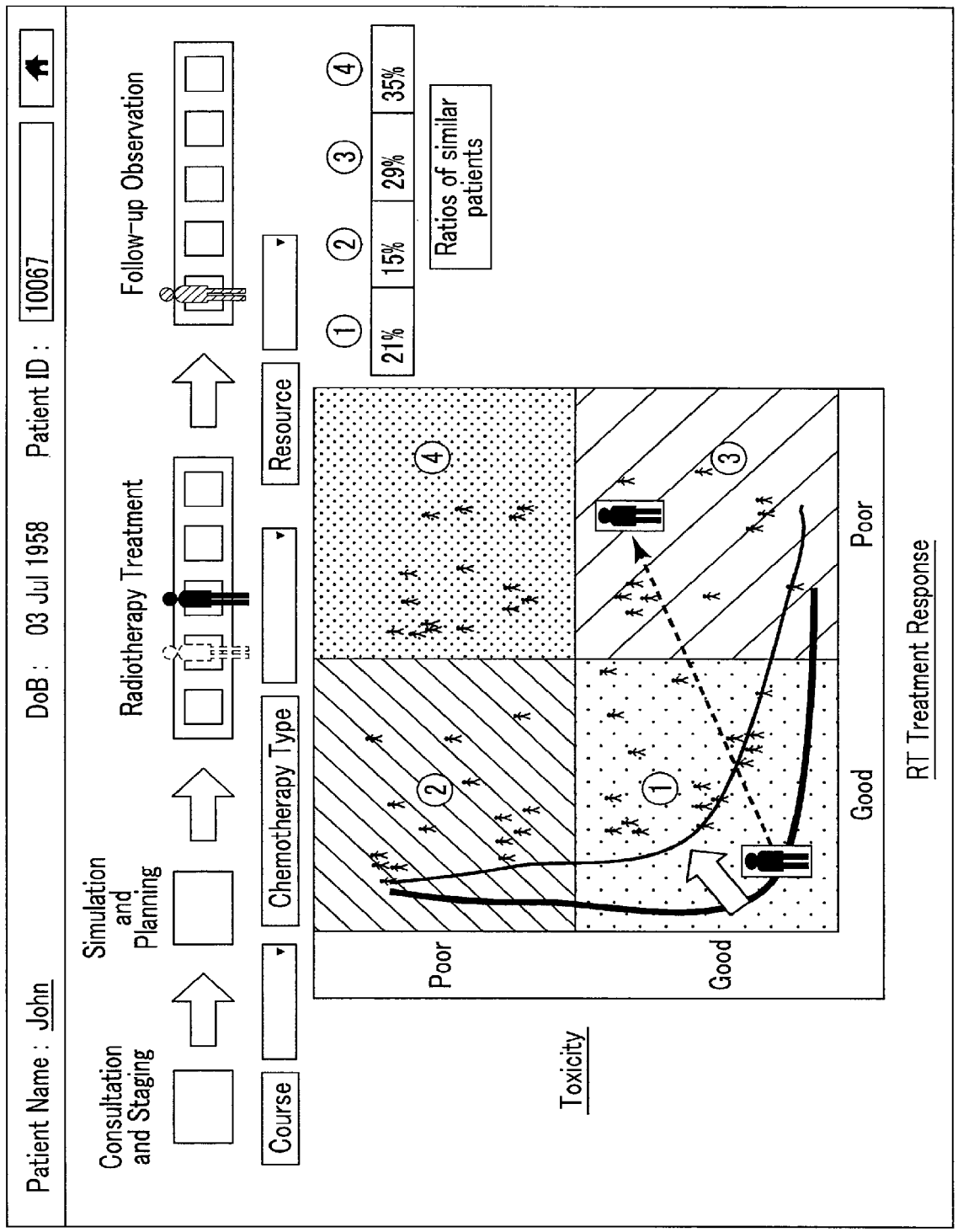
FIG. 23 is a view showing another example of the display image.

FIG. 23 is a view showing an example of a display image generated at a treatment time point indicated at the third square from the left of "Radiotherapy treatment". FIG. 23 shows a change from a display image generated at a treatment time point indicated at the second square from the left of "Radiotherapy treatment". The position of the treatment time point as a basis is expressed by the broken line human figure mark. This allows the doctor to easily grasp a change in the maximum range of selection and predicted changes in treatment result and toxicity with respect to a past treatment time point.

In addition, the first or second embodiment has exemplified the case in which when the operator issues an instruction to move the matched human figure mark added to the area 132 indicating a time point, the control circuitry 15 or 53 executes the display image generation function 154 or 533 to newly generate a display image at a designated check time point. However, this is not exhaustive. For example, the control circuitry 15 or 53 may express, on the second display image, a change from the first display image generated at a check time point as a movement source to the second display image generated at a check time point as a movement destination. For example, this change is displayed as follows.

First of all, the control circuitry 15 or 53 causes the storage circuitry 14 or 52 to store the position of a designated patient in the first display image generated at the check time point as the movement source. The control circuitry 15 or 53 selects similar patients located on the outermost side in the first display image generated at the check time point as the movement source, and connects the selected similar patients with a line. The control circuitry 15 or 53 connects the selected similar patients with a line to express the maximum range of selection by using the line. The control circuitry 15 or 53 causes the storage circuitry 14 or 52 to store the line expressing the maximum rang of selection.

The control circuitry 15 or 53 generates the second display image at the check time point as the movement destination. At this time, the second display image includes a mark indicating the state of the designated patient which is predicted at the check time point as a movement destination and the maximum range of selection which is drawn based on the state of the similar patients at the check time point as the movement source. The control circuitry 15 or 53 superimposes, on the second display image, the line representing the maximum range of selection at the check time point as the movement source and the mark indicating the position of the designated patient at the check time point as the movement source. In addition, the control circuitry 15 or 53 superimposes, on the second display image, an arrow indicating the movement of the maximum range of selection and an arrow indicating the movement of the designated patient. Note that the indication of the movement of the maximum range of selection and the indication of the movement of the designated patient are not limited to arrows as long as it is possible to express movement.

Figure 24:
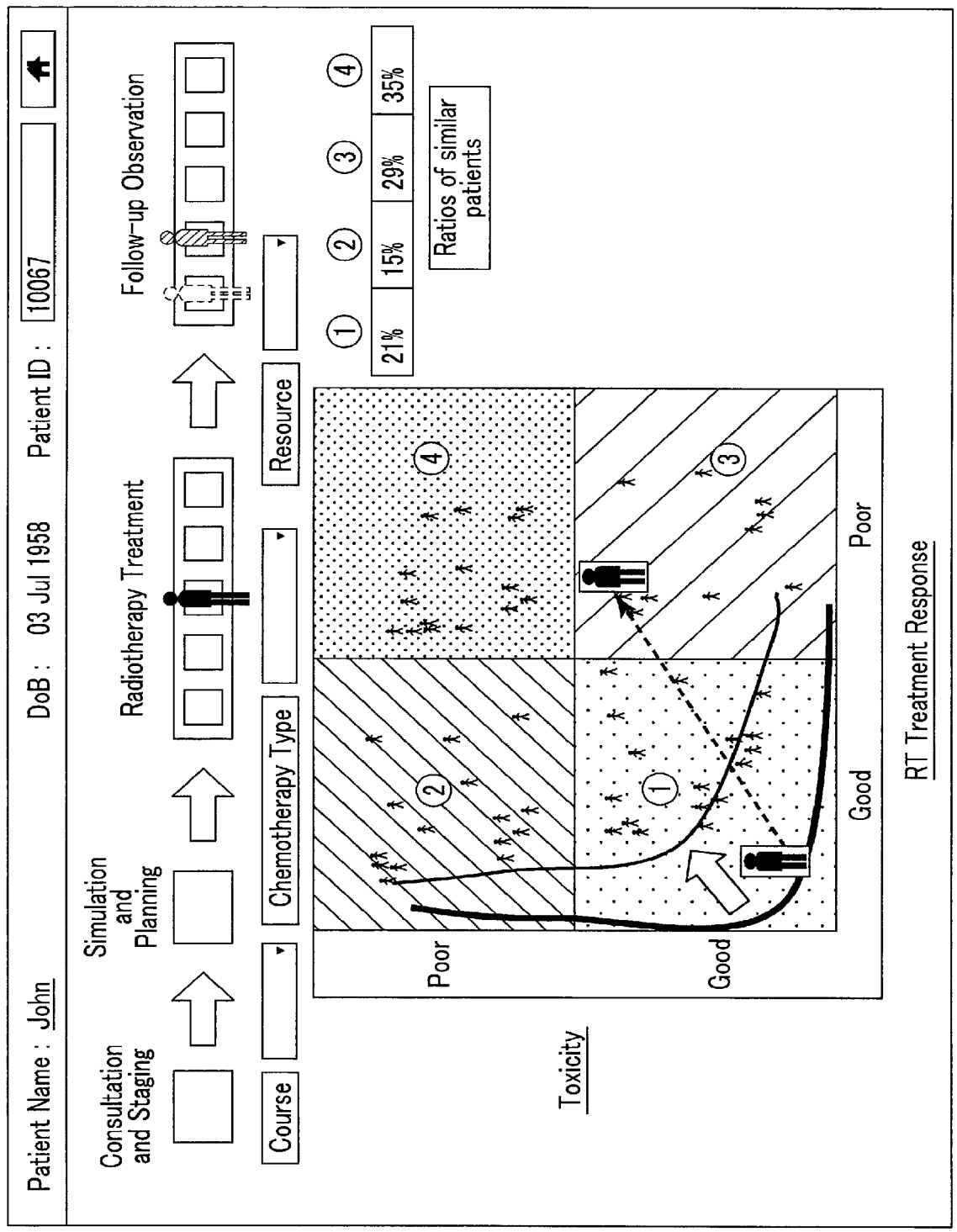
FIG. 24 is a view showing still another example of the display image.

FIG. 24 is a view showing an example of a display image when a human figure mark is moved from the first square from the left of "Follow-up Observation" to the second square. FIG. 24 shows a change from a display image generated at a check time point indicated by the first square from the left of "Follow-up Observation". The position of a check time point as a movement source is represented by a broken line human figure mark. This allows the doctor to easily grasp a change in the maximum range of selection and predicted changes in treatment result and toxicity when the check time point is changed.

In addition, the first or second embodiment has exemplified the case in which the control circuitry 15 or 53 receives an input of a check time point from the prediction function 153 or 532 and calculates a calculation expression for predicting a treatment result and a toxicity at the received check time point. However, this is not exhaustive. A check time point may be recorded on the storage circuitry 14 or 52 in advance, and the control circuitry 15 or 53 may generate a calculation expression for predicting a treatment result and a toxicity at the check time point stored in the storage circuitry 14 or 52.

In addition, the first or second embodiment has exemplified the case in which the control circuitry 15 or 53 executes the display image generation function 154 or 533 to display, in the two-dimensional area 134, similar patients, extracted based on the narrow-down conditions, based on treatment results and toxicities at a check time point. However, this is not exhaustive. The control circuitry 15 or 53 may select similar patients based on treatment statuses. For example, the control circuitry 15 or 53 further selects similar patients having undergone the same treatment stage as that of a designated patient based on the treatment status of the designated patient. More specifically, if a treatment time point for a designated patient corresponds to the completion of third-day irradiation in treatment plan: three-field irradiation (50 Gy/25 times/4 weeks), the control circuitry 15 or 53 further selects similar patients having undergone the same treatment stage as this treatment stage from narrowed-down similar patients or similar patients which have not undergone narrow-down processing. The control circuitry 15 or 53 then generates a display image based on information concerning the selected similar patients. Note that a treatment time point for the designated patient may be input from the input interface circuitry 11.

In addition, the first or second embodiment has exemplified the case in which a patient ID is input as a search key for designating a patient. However, this is not exhaustive. For example, a search key may be a combination of pieces of information included in patient's basic data, e.g., a name and a birth date.

Figure 25:
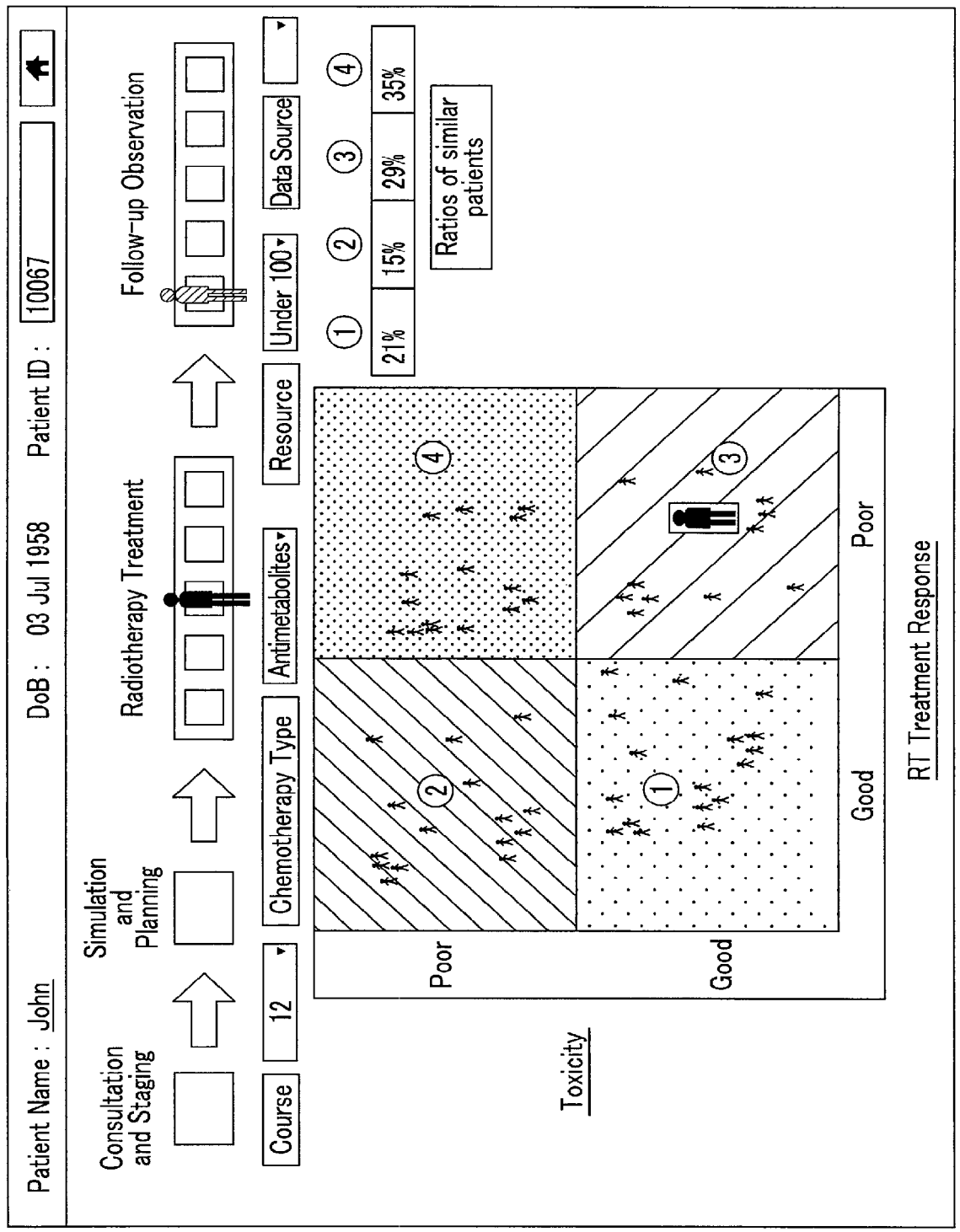
FIG. 25 is a view showing still another example of the display image.

In addition, the first or second embodiment has exemplified "Course", "Chemotherapy Type", and "Resource" as narrow-down conditions. However, they are not exhaustive. As shown in FIG. 25, "data source/locality" may be included in narrow-down conditions. A data source indicates our facility, other facility, or the like. Locality indicates a city, prefecture, country, or the like. Data representing a data source/locality may be included in treatment data.

In addition, the first or second embodiment has exemplified the case in which narrow-down conditions are used to narrow down similar patients arranged in a display image. However, this is not exhaustive. The control circuitry 15 or 53 executes the prediction function 153 or 532 to narrow down data concerning similar patients read out from the storage circuitry 14 or 52 in accordance with narrow-down conditions. The control circuitry 15 or 53 may then generate a calculation expression for predicting a treatment result and a toxicity at a check time point based on data concerning the narrowed-down similar patients.

Figure 26:
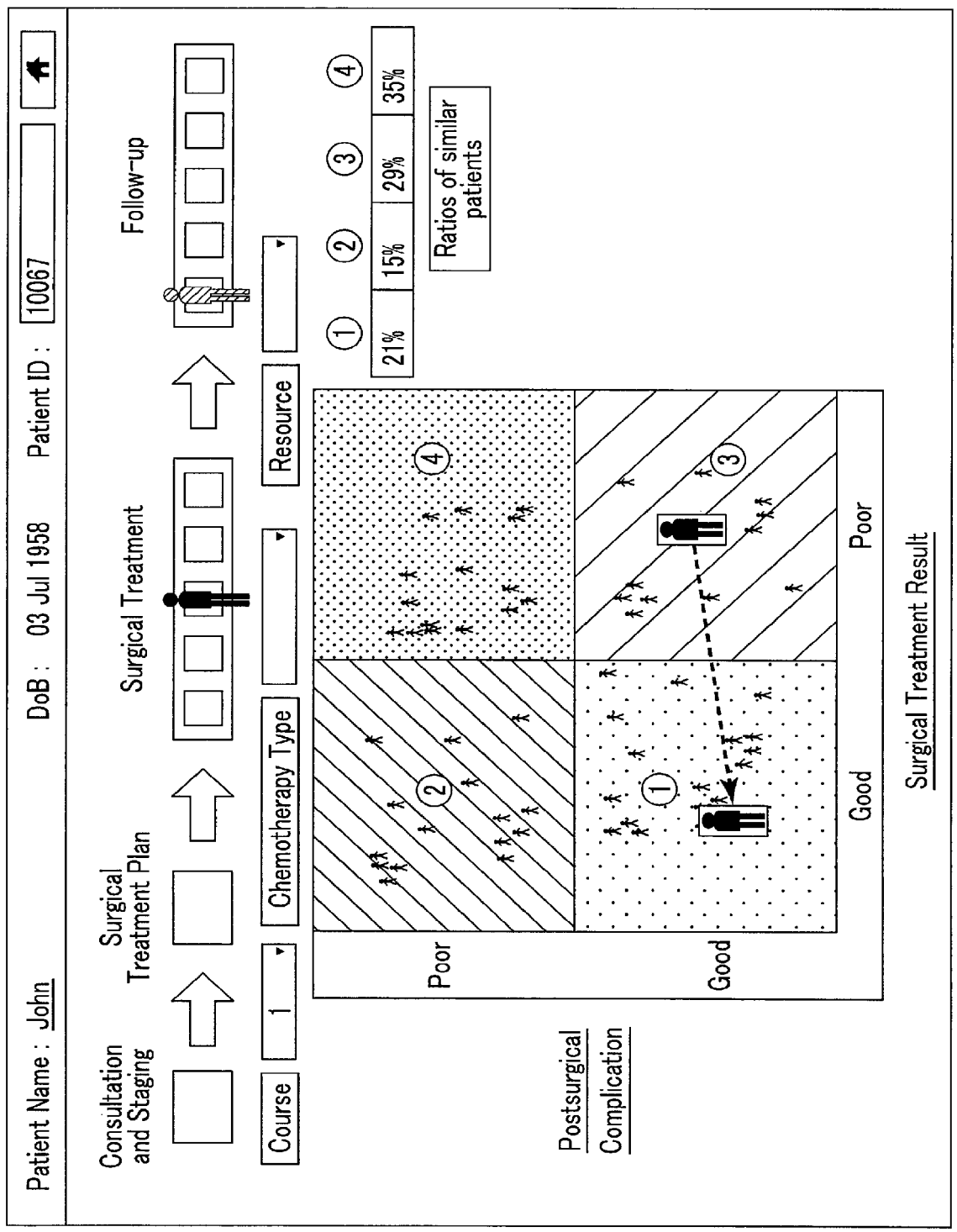
FIG. 26 is a view showing a case in which the medical information processing apparatus is used to decide a treatment plan for a surgical treatment.

Furthermore, the first or second embodiment has exemplified the case in which the medical information processing apparatus 10 or 50 is used for a radiotherapy treatment. However, they may be used for a cancer treatment other than a radiotherapy treatment. For example, as shown in FIG. 26, the medical information processing apparatus 10 or 50 may be used when deciding a treatment plan for a surgical treatment. In addition, for example, as shown in FIG. 27, the medical information processing apparatus 10 or 50 may be used when deciding a treatment plan for a chemotherapy treatment.

Figure 28:
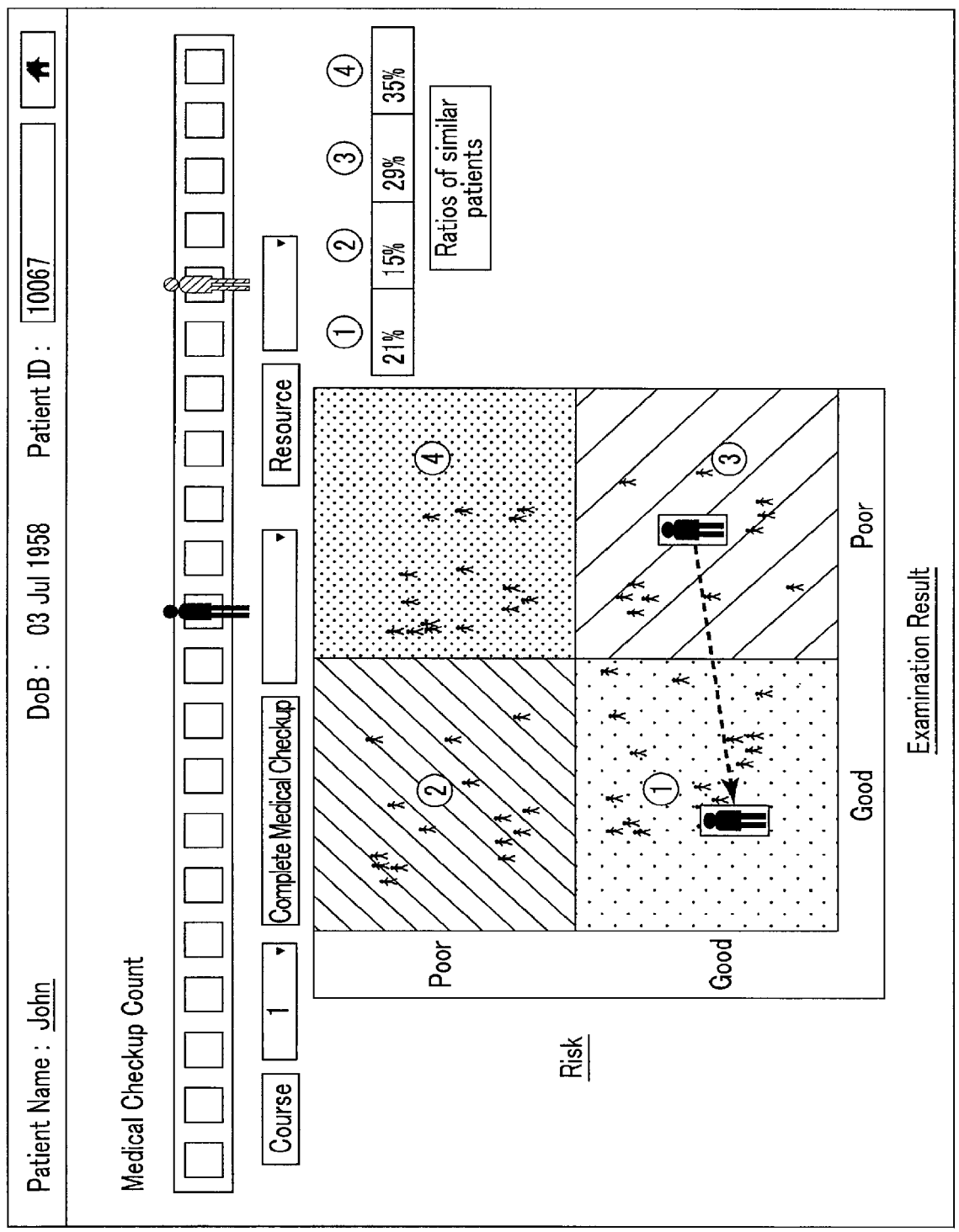
FIG. 28 is a view showing a case in which the medical information processing apparatus is used for disease prevention, based on a health diagnosis result.

Moreover, the first or second embodiment has exemplified the cased in which the medical information processing apparatus 10 or 50 is used for a cancer treatment. However, this is not exhaustive. For example, as shown in FIG. 28, the medical information processing apparatus 10 or 50 may be used for disease prevention based on checkup examination results.

The word "processor" means circuitry such as a CPU (Central Processing Unit), GPU (Graphics Processing Unit), ASIC (Application Specific Integrated Circuit), programmable logic device (e.g., an SPLD (Simple Programmable Logic Device), a CPLD (Complex Programmable Logic Device), or an FPGA (Field Programmable Gate Array)), or the like. The processor implements functions by reading out programs stored in the storage circuitry 14 or 52 and executing them. Note that it is possible to directly incorporate operation programs for the control circuitry 15 or 53 in the circuitry of the processor instead of storing them in the storage circuitry 14 or 52. In this case, the processor implements functions by reading out programs incorporated in the circuitry and executing them. Note that the processor in each embodiment may be formed as one processor by combining a plurality of independent circuitry to implement the data acquisition function, analysis function, prediction function, and display image generation function as well as being formed as single circuitry for each processor.

Although several embodiments have been described above, they are merely examples and not intended to limit the scope of the present invention. These embodiments can be implemented in other various forms, and various omissions, replacements, and changes can be made without departing from the spirit of the present invention. These embodiments and their modifications are incorporated in the scope and sprit of the present invention, and are also incorporated in the scope of the invention and its equivalents defined in the appended claims.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical information processing apparatus comprising:
   processing circuitry configured to
      acquire first information concerning a designated patient,
      acquire second information concerning a similar patient similar to the designated patient,
      obtain a calculation expression based on the second information,
      predict a first value representing a treatment effect and a second value representing a side-effect at a check time point by setting the first information in the calculation expression,
      acquire a third value representing the treatment effect and a fourth value representing the side effect at the check time point based on the second information, and
      generate an interactive map image in which interactive marks representing the designated patient and the similar patient are arranged based on the first to fourth values; and
   a display configured to display the interactive map image,
   wherein the processing circuitry is configured to:
      display selectable marks corresponding to similar patients with at least one of varying treatment results and varying toxicities;

display information of a patient corresponding to a selectable mark when selected; and arrange the marks in corresponding areas of the display according to ranges of effectiveness of treatment and range of toxicity.

2. The apparatus of claim 1, wherein the processing circuitry specifies the similar patient similar to the designated patient based on data concerning patients.

3. The apparatus of claim 1, further comprising input interface circuitry configured to receive a selection instruction for the mark representing the similar patient, wherein
the processing circuitry generates an image displaying detailed information concerning the selected similar patient in accordance with the selection instruction.

4. The apparatus of claim 1, wherein the processing circuitry predicts the first value representing the treatment effect and the second value representing the side effect by substituting information acquired during a treatment of the designated patient into the calculation expression.

5. The apparatus of claim 1, further comprising input interface circuitry configured to receive an input of a narrow down condition, wherein
the processing circuitry acquires the third value representing the treatment effect and the fourth value representing the side effect based on information concerning a similar patient satisfying the narrow down condition.

6. The apparatus of claim 5, wherein the narrow down condition comprises a condition concerning resource management data.

7. The apparatus of claim 1, wherein the similar patient comprises a plurality of similar patients, and
the processing circuitry
acquires the third values representing the treatment effect and the fourth values representing the side-effect at the check time point based on the second information concerning the plurality of similar patients,
generates the map image in which marks representing the designated patient and the plurality of similar patients are arranged based on the first to fourth values,
selects a similar patient for each area set in advance in the map image among the plurality of similar patients, the third value and the fourth value of the selected similar patient being most favorable in the area, and
assigns the selected similar patient with a mark identifiable relative to marks representing other similar patients.

8. The apparatus of claim 1, wherein the processing circuitry displays, in the map image, a change from a map image generated in the past.

9. The apparatus of claim 1, wherein the processing circuitry displays a change from a map image concerning another check time point in the generated map image.

10. The apparatus of claim 1, further comprising input interface circuitry configured to receive a request for detailed information of the third value, wherein
the processing circuitry generates an image displaying the detailed information of the third value in accordance with the request.

11. The apparatus of claim 1, further comprising input interface circuitry configured to receive a request for detailed information of the fourth value, wherein
the processing circuitry generates an image displaying the detailed information of the fourth value in accordance with the request.

12. The apparatus of claim 1, wherein the similar patient comprises a plurality of similar patients, and
the processing circuitry
acquires the third values representing the treatment effect and the fourth values representing the side-effect at the check time point based on the second information concerning the plurality of similar patients,
generates the map image in which marks representing the designated patient and the plurality of similar patients are arranged based on the first to fourth values,
calculates a ratio of the number of similar patients arranged in each area relative to the number of the plurality of similar patients, the areas being set in advance in the map image, and
generates an image displaying the calculated ratios.

13. The apparatus of claim 1, wherein
the similar patient comprises a plurality of similar patients, and
the processing circuitry
selects a similar patient who has undergone a treatment stage corresponding to the designated patient from the plurality of similar patients, and
acquires the third value and the fourth value based on the second information concerning the selected similar patient.

14. The apparatus of claim 1, wherein the processing circuitry is configured to acquire the second information concerning the similar patient similar using one of data analysis and statistical analysis on similar patient data stored in a database.

15. The apparatus of claim 1, wherein the processing circuitry is configured to:
display second marks of different form than the selectable marks in the areas, corresponding to a similar patient progressing most satisfactorily in an area.

16. The apparatus of claim 1, wherein the processing circuitry is configured to:
display a corresponding treatment plan when a selectable mark is selected.

17. The apparatus of claim 1, wherein the processing circuitry is configured to:
display movable marks along with the selectable marks, the movable marks being configured to be moved by dragging and dropping by a user.

* * * * *